US006887906B1

(12) United States Patent
Teng et al.

(10) Patent No.: US 6,887,906 B1
(45) Date of Patent: May 3, 2005

(54) COMPOSITIONS AND METHODS FOR THE DELIVERY OF OLIGONUCLEOTIDES VIA THE ALIMENTARY CANAL

(75) Inventors: Ching-Leou Teng, San Diego, CA (US); Greg Hardee, Rancho Santa Fe, CA (US)

(73) Assignee: ISISPharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 09/108,673

(22) Filed: Jul. 1, 1998

Related U.S. Application Data

(63) Continuation-in-part of application No. 08/886,829, filed on Jul. 1, 1997.

(51) Int. Cl.[7] .................. A61K 47/00; A61K 31/70; A01N 25/00; C07H 21/04
(52) U.S. Cl. .................. 514/784; 514/946; 514/44; 536/23.1; 536/24.5
(58) Field of Search .................. 424/450; 435/6; 514/44, 784, 946; 536/23.1, 24.5

(56) References Cited

U.S. PATENT DOCUMENTS

| | | | | |
|---|---|---|---|---|
| 4,689,320 | A | 8/1987 | Kaji | 514/44 |
| 4,806,463 | A | 2/1989 | Goodchild et al. | 435/5 |
| 4,835,263 | A | 5/1989 | Nguyen et al. | 536/27 |
| 5,004,810 | A | 4/1991 | Draper | 536/27 |
| 5,034,506 | A | 7/1991 | Summerton et al. | 528/391 |
| 5,087,617 | A | 2/1992 | Smith | 514/44 |
| 5,098,890 | A | 3/1992 | Gewirtz et al. | 514/44 |
| 5,135,917 | A | 8/1992 | Burch | 514/44 |
| 5,138,045 | A | 8/1992 | Cook et al. | 536/27 |
| 5,166,195 | A | 11/1992 | Ecker | 514/44 |
| 5,194,428 | A | 3/1993 | Agrawal et al. | 514/44 |
| 5,212,295 | A | 5/1993 | Cook | 536/26.7 |
| 5,218,105 | A | 6/1993 | Cook et al. | 536/25.31 |
| 5,242,906 | A | 9/1993 | Pagano et al. | 514/44 |
| 5,264,423 | A | 11/1993 | Cohen et al. | 514/44 |
| 5,276,019 | A | 1/1994 | Cohen et al. | 514/44 |
| 5,286,717 | A | 2/1994 | Cohen et al. | 514/44 |
| 5,298,614 | A | 3/1994 | Yano et al. | 536/25.5 |
| 5,378,825 | A | 1/1995 | Cook et al. | 536/25.34 |
| 5,386,023 | A | 1/1995 | Sanghvi et al. | 536/25.3 |
| 5,455,335 | A | 10/1995 | Kahne et al. | 536/5 |
| 5,457,191 | A | 10/1995 | Cook et al. | 536/27.13 |
| 5,459,255 | A | 10/1995 | Cook et al. | 536/27.13 |
| 5,506,351 | A | 4/1996 | McGee | 536/55.3 |
| 5,521,302 | A | 5/1996 | Cook | 536/25.31 |
| 5,539,082 | A | 7/1996 | Nielsen et al. | 530/300 |
| 5,539,083 | A | 7/1996 | Cook et al. | 530/333 |
| 5,541,307 | A | 7/1996 | Cook et al. | 536/23.1 |
| 5,543,508 | A | 8/1996 | Haseloff et al. | 435/365 |
| 5,545,729 | A | 8/1996 | Goodchild et al. | 536/24.5 |
| 5,554,746 | A | 9/1996 | Ravikumar et al. | 540/200 |
| 5,571,902 | A | 11/1996 | Ravikumar et al. | 536/22.1 |
| 5,578,718 | A | 11/1996 | Cook et al. | 536/27.21 |
| 5,587,361 | A | 12/1996 | Cook et al. | 514/44 |
| 5,587,469 | A | 12/1996 | Cook et al. | 536/23.1 |
| 5,587,470 | A | 12/1996 | Cook et al. | 536/23.1 |
| 5,591,721 | A | 1/1997 | Agrawal et al. | 514/44 |
| 5,595,978 | A | 1/1997 | Draper | 514/44 |
| 5,599,797 | A | 2/1997 | Cook et al. | 514/44 |
| 5,602,240 | A | 2/1997 | De Mesmaeker et al. | 536/22.1 |
| 5,608,046 | A | 3/1997 | Cook et al. | 536/23.1 |
| 5,610,289 | A | 3/1997 | Cook et al. | 536/25.34 |
| 5,707,648 | A | * 1/1998 | Yiv | 424/450 |
| 5,780,444 | A | 7/1998 | Kahne | 514/26 |
| 5,843,738 | A | * 12/1998 | Bennett et al. | 435/455 |
| 5,948,898 | A | 9/1999 | Dean et al. | 536/23.5 |
| 5,955,059 | A | 9/1999 | Gilchrest et al. | 424/59 |
| 5,994,062 | A | * 11/1999 | Mulshine et al. | 435/6 |
| 6,096,722 | A | * 8/2000 | Bennett et al. | 514/44 |

FOREIGN PATENT DOCUMENTS

| | | | |
|---|---|---|---|
| JP | 57080314 | * 5/1982 | 424/400 |
| WO | WO 92/20813 | 11/1992 | |
| WO | WO92/21353 | 12/1992 | |
| WO | WO 93/19660 | 10/1993 | |
| WO | WO 93/24510 | 12/1993 | |
| WO | WO 94/00155 | 1/1994 | |
| WO | WO94/18835 | 9/1994 | |
| WO | WO 95/11748 | 5/1995 | |
| WO | WO 96/12497 | 5/1996 | |
| WO | WO 96/30051 | 10/1996 | |

(Continued)

OTHER PUBLICATIONS

Orkin et al. Report and recommendations of the panel to assess the NIH investment in research on gene therapy. 1995, p. 1–20.*

Agrawal et al. Antisense therapeutics: Is it as simple as complementary base recognition? Molecular Medicine Today, vol. 6:72–81, Feb. 2000.*

(Continued)

*Primary Examiner*—David Guzo
*Assistant Examiner*—Quang Nguyen
(74) *Attorney, Agent, or Firm*—ISIS Pharmaceuticals, Inc.; Cozen O'Connor

(57) ABSTRACT

The present invention relates to compositions and methods which enhance the transport of nucleic acids, especially oligonucleotides at various sites in the alimentary canal of an animal. The methods and compositions enhance the transport of oligonucleotides across the mucosa of the alimentary canal via the use of one or more penetration enhancers. The invention features the use of various fatty acids, bile salts, chelating agents and other penetration enhancers, as well as carrier compounds, to enhance the stability of nucleic acids and/or their transport across and/or into cells of the alimentary canal. In one preferred embodiment, the compositions and methods of the invention are utilized to effect the oral delivery of an antisense oligonucleotide to an animal in order to modulate the expression of a gene in the animal for investigative, therapeutic or prophylactic purposes.

4 Claims, No Drawings

FOREIGN PATENT DOCUMENTS

| WO | WO 96/32496 | 10/1996 | | |
|---|---|---|---|---|
| WO | WO 96/34008 | 10/1996 | | |
| WO | WO 96/41011 | 12/1996 | | |
| WO | WO 97/05903 | 2/1997 | | |
| WO | WO97/05903 | * 2/1997 | ................ | 424/709 |
| WO | WO 97/12995 | 4/1997 | | |
| WO | WO98/00110 | 1/1998 | | |
| WO | WO98/33932 | 8/1998 | | |
| WO | WO 98/49348 | 11/1998 | | |
| WO | WO99/01579 | 1/1999 | | |

OTHER PUBLICATIONS

Branch A good antisense molecule is hard to find. TIBS, vol. 23:45–50, Feb. 1998.*

Rojanasakul, Y. Antisense oligonucleotide therapeutics: Drug delivery and targeting. Advanced Drug Delivery Reviews. vol. 18:115–131, Jan. 1996.*

Nolen, H.W., et al., "Percutaneous penetration of methyl phosphonate antisense oligonucleotides," Intl. J. Pharm. (1994) 107:169–177.

Miller, K., et al., "In vitro transdermal flux and tissue distribution of interleukin 1 beta antisense methyl phosphonate oligonucleotide from topical formulations," Pharm. Res. (1993) 10: (Supp 1) S252.

Lieb, L.M., et al., "Follicular permeation of oligonucleotides," Proc. Controlled Release Soc. (1995) 22:654–655.

Nolen, H. W., "Percutaneous penetration of methyl phosphonate antisense oligonucleotides," *International J Pharmaceutics*, 1994, 107, 169–177.

Walker, S., et al., "Catioinic facial amphiphiles: A promising class of transfection agents," *Proc. Natl. Acad. Sci. USA*, 1996, 93, 1585–1590.

Akamo, Y. et al., "Chemotherapy Targeting Regional Lymph Nodes by Gastric Submucosal Injection of Liposomal Adriamycin in Patients with Gastric Carinoma", *Japanese J. Cancer Res.*, 1994, 85, 652–658.

Albert, P.R. et al., "Antisense knockouts: molecular scalpels for the dissection of signal transduction", *Trends Pharmacol. Sci.*, 1994, 15, 250–254.

Anonymous, "ISIS Pharmaceuticals Demonstrates Efficacy In Chrohn's Disease with its Antisense Drug", *Genetic Engineer. News.*, 1997, pp. 1 and 34.

Aungst, B.J. et al., "Site Dependence of Absorption–Promoting Actions of Laureth–9, Na Salicylate, Na₂EDTA, and Aprotinin on Rectal, Nasal, and Buccal Insulin Delivery", *Pharm. Res.*, 1988, 5, 305–308.

Ausubel et al. (eds.), *Short Protocols in Molecular Biology*, 2d Ed., John Wiley and Sons, New York, NY, Chapter 3, 3–11 to 3–38.

Bailly, C. et al., "PCR–based development of DNA substrates containing modified bases: An efficient system for investigating the role of the exocyclic groups in chemical and structural recognition by minor groove binding drugs and proteins", *Proc. Natl. Acad. Sci. USA.*, 1996, 93, 13623–13628.

Beck, S., "Nonradioactive Detection of DNA Using dioxetane Chemiluminescence", *Methods in Enzymology*, 1992, 216, 143–153.

Benet et al., Pharmacokinetics: The Dynamics of Drug Absorption, Distribution, and Elimination, *Goodman & Gilman's The Pharmacological Basis of Therapeutics*, 9th Ed., Hardman et al. (eds.), McGraw–Hill, New York, NY, 1996, Chapter 1, 3–9.

Berge, S.M. et al., "Pharmaceutical Salts", *J. Pharm. Sci.*, 1977, 66, 1–19.

Block, L., "Medicated Applications", *Remington's Pharmaceutical Sciences*, 18th Ed., Gennaro (ed.), Mack Publishing Co., Easton, PA, 1990, Ch. 87, 1596–1614.

Brunton, L.L., "Agents Affecting Gastrointestinal Water Flux and motility; Emesis and Antiemetics; Bile Acids and Pancreatic Enzymes", *Goodman & Gilman's The Pharmacological Basis of Therapeutics*, 9th Ed., Hardman et al. (eds.), McGraw–Hill, New York, 1996, Chapter 38, 934–935.

Buur, A. et al., "Penetration of 5–Fluorouracil and prodrugs across the intestine of the albino rabbit: Evidence for shift in absorption site from the upper to the lower region of the gastrointestinal tract by prodrugs", *J. Controlled Release*, 1990, 14, 43–51.

Buzayan, J.M. et al., "Satellite tobacco ringspot virus RNA: A subset of the RNA sequence is sufficient for autolytic processing", *Proc. Natl. Acad. Sci. USA*, 1986, 83, 8859–8862.

Chollet, A. et al., "DNA containing the base analogue 2–aminoadenine: preparation, us as hybridization probes and cleavage by restriction endonucleases", *Nucl. Acids Res.*, 1988, 16, 305–317.

Constantinides, P.P. et al., "Formulation and Intestinal Absorption Enhancement Evaluation of Water–in–Oil Microemulsions Incorporating Medium–Chain Glycerides", *Pharm. Res.*, 1994, 11, 1385–1390.

Crooke, S.T., "Progress in Antisense Therapeutics", *Hematologic Pathology*, 1995, 9, 59–72.

Crooke, S.T. et al., "Progress in the development and patenting of antisense drug discovery technology", *Exp. Opin. Ther. Patents*, 1996, 6, 855–870.

Crooke, S.T. et al., "Pharmacokinetic Properties of Several Novel Oligonucleotide Analogs in mice", *J. Pharmacol. Exp. Ther.*, 1996, 277, 923–937.

Dean, N.M. et al., "Inhibition of protein kinase C–α expression in mice after systemic administration of phosphorothiate antisense oligodeoxynucleotides", *Proc. Natl. Acad. Sci. USA*, 1994, 91, 11762–11766.

DeVries, M.H. et al., "Decarboxylation of L–Dopa in the Rat Isolated Vascularly perfused Small Intestine: Contribution to Systemic Elimination and Dose–dependent First Pass Effect", *J. Pharm. Pharmacol.*, 1992, 44, 311–314.

DiSanto, A.R., "Bioavailability and Bioequivalency Testing", *Remington's Pharmaceutical Sciences*, 18th Ed., Gennaro (ed), Mack Publishing Co., Easton, PA, 1990, Ch. 76, 1451–1458.

El–Hariri, L.M. et al., "The Mitigating Effects of Phosphatidylcholines on Bile Salt–and Lysophosphatidylcholine–induced Membrane Damage", *J. Pharm. Pharmacol.*, 1992, 44, 651–654.

Forster, A.C. et al., "Self–Cleavage of Virusoid RNA is Performed by the Proposed 55–Nucleotide Active Site", *Cell*, 1987, 50, 9–16.

Gaffney, B.L. et al., The Influence of the Purine 2–Amino Group on DNA Conformation and Stability–II *Tetrahedron*, 1984, 40, 3–13.

Gebeyehu, G. et al., "Novel biotinylated nucleotide—analogs for labelling and colorimetric detection of DNA", *Nucl. Acids Res.*, 1987, 15, 4513–4534.

Graham, M.J. et al., "Tritium labeling of antisense oligonucleotides by exchange with tritiated water", *Nucl. Acids Res.*, 1993, 21, 3737–3743.

Harvey, S.C., "Drug Absorption, Action, and Disposition", *Remington's Pharmaceutical Sciences*, 18th Ed., Gennaro (ed.), Mack Publishing Co., Easton, PA,. 1990, Ch. 35, 711–715.

Hirahata et al., *Gan To Kagaku Ryoho*, 1992, *19(10 Suppl.)*, 1591–1594 (English abstract included).

Ho, H.O. et al., "Preparation of Microemulsions Using Polyglycerol Fatty Acid Esters as Surfactant for the Delivery of Protein Drugs", *J. Pharm. Sci.*, 1996, 85, 138–143.

Ho, N.F.H et al., "Theoretical Model Studies of Drug Absorption and Transport in the GI Tract III", *J. Pharm. Sci.*, 1972, 61, 192–197.

Inoue, Y. et al., "Trail of Electrolyzed Strong Acid Aqueous Solution Lavage in the treatment of Peritonitis and Intraperitoneal Abscess", *Artificial Organs*, 1997, 21, 28–31.

Iverson, P. et al., "In vivo studies with phosphorothioate oligonucleotides: pharmacokinetics prologue", *Anti–Cancer Drug Des.*, 1991, 6, 531–538.

Jarrett, H.W., "Affinity chromatography with nucleic acid polymers", *J. Chromatography*, 1993, 618, 315–339.

Kabanov, A.V. et al., "A new class of antivirals" antisense oligonucleotides combined with a hydrophobic substituent effectively inhibit influenza virus reproduction and synthesis of virus–specific proteinsin MDCK cells, *FEBS Letts.*, 1990, 259, 327–330.

Kararli, T.T. et al., "Oral Delivery of a Renin Inhibitor Compound Using Emulsion Formulations", *Pharmaceutical Res.*, 1992, 9, 888–893.

Katocs, A.S. et al., "Biological Testing", *Remington's Pharmaceutical Sciences*, 18th Ed., Gennaro (ed.), Mack Publishing Co., Easton PA, 1990, Ch. 27, 484–494.

Komiya, I. et al., "Quantitative Mechanistic Studies in Simultaneous Fluid Flow And Intestinal Absorption Using Steroids As Model Solutes", *Int. J. Pharmaceut.*, 1980, 4, 249–262.

Kornberg, A., *DNA Replication*, W.H. Freeman and Co., San Francisco, 1980, 4–7, 75–77.

Lee, V.H.L. et al., "Mucosal Penetration Enhancers For Facilitation of Peptide and Protein Drug Absorption", *Crit. Rev. Ther. Drug Carrier Systems*, 1991, 8, 91–92.

Letsinger, R.L. et al., "Cholesteryl–conjugated oligonucleotides: Synthesis, properties, and activity as inhibitors of replication of human immunodeficiency virus in cell culture", *Proc. Natl. Acad. Sci. USA*, 1989, 86, 6553–6556.

Longer, M.A. et al., "Sustained–Release Drug Delivery Systems", *Remington's Pharmaceutical Sciences*, 18th Ed., Gennaro (ed.), Mack Publishing Co., Easton, PA, 1990, Ch. 91, 1676–1693.

Manoharan, M. et al., "Cholic Acid–Oligonucleotide Conjugates for Antisense Applications", *Boorg. Med. Chem. Letts.*, 1994, 4, 1053–1060.

Manoharan, M. et al., "Chemical Modifications to Improve Uptake and Bioavailability of Antisense Oligonucleotides", *Ann. N.Y. Acad. Sci.*, 1992, 660, 306–309.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan, M. et al., "Lipidic Nucleic Acids", *Tetrahedron Letts.*, 1995, 36, 3651–3654.

Manoharan, M. et al., "Oligonucleotide conjugates: Alternation of the Pharmacokinetic Properties of Antisense Agents", *Nucleosides & Nucleotides*, 1995, 14, 969–973.

Martin, P., "Ein neuer Zugang zu 2'–O–Alkylribonucleosiden und Eigneschaften deren Oligonucleotide", *Helvetica Chemica Acta*, 1995, 78, 486–504 (English summary included).

Mishra, R.K. et al., "Improved leishmanicidal effect of phosphorotioate antisense oligonucleotides by LDL–mediated delivery", *Biochim. Biophys. Acta*, 1995, 1264, 229–237.

Miyao, T. et al., "Stability and Pharmacokinetic Characteristics of Oligonucleotides Modified at terminal Linkages in Mice", *Antisense Res. Dev.*, 1995, 5, 115–121.

Muranishi, S., "Absorption Enhancers", *Crit. Rev. Ther. Drug Carrier Systems*, 1990, 7, 1–33.

Nairn, J.G., "Solutions, Emulsions, Suspensions and Extracts", *Remington's Pharmaceutical Sciences*, 18th Ed., Gennaro (ed.), Mack Publishing Co., Easton, PA, 1990, Ch. 83, 1519–1544.

Nielsen, P.E. et al., "Sequence–Selective Recognition of DNA by Strand Displacement with a Thymine–Substituted Polyamide", *Science*, 1991, 254, 1497–1500.

Nies, A.S. et al., "Principles of Therapeutics", *Goodman & Gilman's The Pharmacological Basis of Therapeutics*, 9th Ed., Hardman et al. (ed.), McGraw–Hill, New York, NY, 1996, Ch. 3, 43–62.

Oberhauser, B. et al., "Effective incorporation of 2'–O–methyl–oligoribonucleotides into liposomes and enhanced cell association through modification with thiocholesterol", *Nucl. Acids Res.*, 1992, 20, 533–538.

Pennington, C.R. et al., "Review article: artificial nutritional support for patient care", *Ailment Pharamacol. Ther.*, 1995, 471–481.

Plenat, F. et al., "Animal models of antisense oligonucleotides: lessons for use in humans", *Mol. Med. Today*, Jun. 1996, 250–257.

Porter, S.C., "coating of Pharmaceutical Dosage Forms", *Remington's Pharmaceutical Sciences*, 18th Ed., Gennaro (ed.), Mack Publishing Co., Easton, PA, 1990, Ch. 90, 1666–1675.

Powell, J.J. et al., "Intestinal perfusion of dietary levels of aluminium: association with the mucosa", *Gut*, 1994, 35, 1053–1057.

Prosnyak, M.I. et al., "Substitution of 2–Aminoadenine and 5–Methylcytocsine for Adenine and Cytosine in Hybridization Probes Increases the Sensitivity of DNA Fingerprinting", *Genomics*, 1994, 21, 490–494.

Robertson, D., "Crohn's trial shows the pros of antisense", *Nature Biotechnology*, 1997, 15, 209.

Rudnic, E. et al., "Oral Solid Dosage Forms", *Remington's Pharmaceutical Sciences*, 18th Ed., Gennaro (ed.), Mack Publishing Co., Easton, PA, 1990, Ch. 89, 1633–1665.

Ruth, J.L., "Oligonucleotide–Enzyme Conjugates" *Methods of Molecular Biology*, Agrawal, S. (ed.), Human Press, Totowa, NJ, 1994, Chapter 6, 167–185.

Saison–Behmoaras, T. et al., "Short modified antisense oligonucleotides directed against Ha–ras point mutation induce seledctive cleavage of the mRNA and inhibit T24 cells proliferation", *EMBO J.*, 1991, 10, 1111–1118.

Sambrook et al. (eds.), "Preparation of Radiolabeled DNA and RNA Probes", *Molecular Cloning: A Laboratory Manual*, 2d. Ed., Chapter 10, 10.1 to 10.70.

Shea, R.G. et al., "Synthesis, hybridization properties and antiviral activity of lipid–oligonucleotide conjugates", *Nucl. Acids Res.*, 1990, 18, 3777–3783.

Smith, L.M., "Automated Synthesis and Sequence Analysis of Biological Macromolecules", *Anal. Chem.*, 1988, 60, 381A–390A.

Somogyi, A.A. et al., "Evaluation of the Intestinal Absorption of Erythromycin in Man: Absolute Bioavailability Comparison with Enteric Coated Erythromycin", *Pharm. Res.*, 1995, 12, 149–154.

Svinarchuk, F.P. et al., "Inhibition of HIV proliferation in MT–4 cells by antisense oligonucleotide conjugated to lipophilic groups", *Biochimie*, 1993, 75, 49–54.

Swinyard, E.A., "Gastrointesinal Drugs", *Remington's Pharmaceutical Sciences*, 18th Ed., Gennaro (ed.), Mack Publishing Co., Easton, PA, 1990, Ch. 39, 782–783.

Takahasi, H. et al., "The Use of a Perfluorochemical Emulsion as a Bascular Perfusate in Drug Absorption", *J. Pharm. Pharmacol.*, 1988, 40, 252–257.

Takakura, Y. et al., "Uptake Characteristics of Oligonucleotides in the Isolated Rat Liver Profusion System", *Antisense Nucl. Acid Drug Dev.*, 1996, 6, 177–173.

U.S. Congress, Office of Technology Assessment, Genetic Monitoring and Screening in the Workplace, OTA–BA–455, U.S. Government Printing Office, Washington, D.C., 1990, Ch. 5, 75–99.

van Berge–Henegouwen, G.P. et al., "Pharmacology of Chenodeoxycholic Acid. II. Absorption and metabolism", *Gastroenterol.*, 1977, 73, 300–309.

Wahlestedt, C. et al., "Antisense oligodeoxynucleotides to NMDA–R1 receptor channel protect cortical neurons from excitotoxicity and reduce focal ischaemic infarctions", *Nature*, 1993, 363, 260–263.

Wahlestedt, C. et al., "Modulation of Anxiety and Neuropeptide Y–Y1 Receptors by antisense Oligodeoxynucleotides", *Science*, 1993, 259, 528–531.

Warren, W.J. et al., "Protocols for Oligonucleotides Conjugates", *Methods in Molecular Biology*, Agrawal, S. (ed.), Humana Press, Totowa, NJ, 1994, vol. 26, Chapter 9, 233–264.

Yamamoto, A. et al., "A Mechanistic study on Enhancement of Rectal Permeability to Insulin in the Albino Rabbit", *J. Pharm. Exp. Ther.*, 1992, 263, 25–31.

Yamashita, S. et al., "Effect of Adjubants on charge–Selective Permeability and Electrical Resistance of Rat Jejunal Membrane", *J. Pharm. Sci.*, 1990, 79, 579–853.

Yamashita, S. et al., "Effects of diclofenac sodium and disodium ethylenediaminetetraacetate on electrical parameters of the mucosal membrane and their relation to the permeability enhancing effects in the rat jejunum", *J. Pharm. Pharmacol.*, 1987, 39, 621–626.

Yamashita, S. et al., "Kinetic Analysis of the Drug Permeation Process Across the Intestinal Epithelium", *Pharm. Res.*, 1994, 11, 1646–1651.

Gerwirtz et al., "Facilitating oligonucleotide delivery: Helping antisense deliver in its promise", *PNAS (USA)*, 1996, 93, 3161–3163.

Gura, T., "Antisense has growing pains. Efforts to develop antisense compounds as therapies for cancer, AIDS, and other diseases have encountered some unexpected questions about how the drugs really work", *Science*, 1995, 270, 575–577.

Stull et al., "Antigene, ribozyme and aptamer nucleic acid drugs: progress and prospects", *Pharm. Res.*, 1995, 12(4), 465–483.

Baker, B.F. et al., "Cleavage of the 5' Cap Structure of mRNA by a Europium(III) Macrocyclic Complex with Pendant Alcohol Groups", *J. Am. Chem. Soc.*, 1997, 119(38), 8749–8755.

Chiang, M.Y. et al., "Antisense Oligonucleotides Inhibit Intercellular Adhesion Molecule 1 Expression by Two Distinct Mechanisms", *J. Biol. Chem.*, 1991, 266, 18162–18171.

Forster, A.C. et al., "External Guide Sequences for an RNA Enzyme", *Science*, 1990, 249, 783–786.

Haseloff, J. et al., "Simple RNA enzymes with new and highly specific endoribonuclease activities", *Nature*, 1988, 334, 585–591.

* cited by examiner

SEQUENCE LISTING (1) GENERAL INFORMATION:

(iii) NUMBER OF SEQUENCES: 132

(2) INFORMATION FOR SEQ ID NO: 1:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: ISIS 2302

(x) PUBLICATION INFORMATION:
        (H) DOCUMENT NUMBER: US 5591623 (SEQ ID NO:22)
        (I) FILING DATE: 21-JAN-1993
        (J) PUBLICATION DATE: 07-JAN-1997

(xi) SEQUENCE DESCRIPTION:  SEQ ID NO: 1:

GCCCAAGCTG GCATCCGTCA                                                    20

(2) INFORMATION FOR SEQ ID NO: 2:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: GM1595

(x) PUBLICATION INFORMATION:
        (H) DOCUMENT NUMBER: US 5580969 (SEQ ID NO:11)
        (I) FILING DATE: 12-OCT-1993
        (J) PUBLICATION DATE: 12-DEC-1996

(xi) SEQUENCE DESCRIPTION:  SEQ ID NO: 2:

AGCCATAGCG AGGCTGAGGT T                                                  21

(2) INFORMATION FOR SEQ ID NO: 3:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: ISIS 5847

(x) PUBLICATION INFORMATION:
        (H) DOCUMENT NUMBER: US 5591623 (SEQ ID NO:72)
        (I) FILING DATE: 21-JAN-1993
        (J) PUBLICATION DATE: 07-JAN-1997

(xi) SEQUENCE DESCRIPTION:  SEQ ID NO: 3:

AACATCTCCG TACCATGCCA                                                    20

(2) INFORMATION FOR SEQ ID NO: 4:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: GM1535

(x) PUBLICATION INFORMATION:
            (H) DOCUMENT NUMBER: US 5596090 (SEQ ID NO:3)
            (I) FILING DATE: 12-OCT-1993
            (J) PUBLICATION DATE: 21-JAN-1997

(xi) SEQUENCE DESCRIPTION:   SEQ ID NO: 4:

CCCAGGCATT TTAAGTTGCT G                                            21

(2) INFORMATION FOR SEQ ID NO: 5:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: GM1515

(x) PUBLICATION INFORMATION:
            (H) DOCUMENT NUMBER: US 5585479 (SEQ ID NO:1)
            (I) FILING DATE: 12-OCT-1993
            (J) PUBLICATION DATE: 17-DEC-1996

(xi) SEQUENCE DESCRIPTION:   SEQ ID NO: 5:

GTTTAAGGCA GCATCCTAAG A                                            21

(2) INFORMATION FOR SEQ ID NO: 6:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: GM1516

(x) PUBLICATION INFORMATION:
            (H) DOCUMENT NUMBER: US 5585479 (SEQ ID NO:2)
            (I) FILING DATE: 12-OCT-1993
            (J) PUBLICATION DATE: 17-DEC-1996

(xi) SEQUENCE DESCRIPTION:   SEQ ID NO: 6:

TCACCCAAAG GTTTAGGCTT G                                            21

(2) INFORMATION FOR SEQ ID NO: 7:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:

-continued (D) OTHER INFORMATION: GM1517

(x) PUBLICATION INFORMATION:
         (H) DOCUMENT NUMBER: US 5585479 (SEQ ID NO:3)
         (I) FILING DATE: 12-OCT-1993
         (J) PUBLICATION DATE: 17-DEC-1996

(xi) SEQUENCE DESCRIPTION:   SEQ ID NO: 7:

GCAATCATGA CTTCAAGAGT T                                                    21

(2) INFORMATION FOR SEQ ID NO: 8:

(i) SEQUENCE CHARACTERISTICS:
         (A) LENGTH: 18 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to c-myb mRNA; a.k.a.
             "MYB-AS"

(x) PUBLICATION INFORMATION:
         (A) AUTHORS: Calabretta, Bruno, et al.
         (B) TITLE: Inhibition of Protooncogene Expression in Leukemic
             Cells: An Antisense Approach
         (C) JOURNAL: Antisense Research and Applications,
             Crooke, S.T., et al., eds., CRC Press, Boca Raton
         (D) VOLUME: Chapter 31
         (F) PAGES: 535-545
         (G) DATE: 1993

(xi) SEQUENCE DESCRIPTION:   SEQ ID NO: 8:

GTGCCGGGGT CTTCGGGC                                                        18

(2) INFORMATION FOR SEQ ID NO: 9:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to mammalian DNA
             methyl transferase (x) PUBLICATION INFORMATION:
         (H) DOCUMENT NUMBER: WO 95/15378 (SEQ ID NO:1)
         (I) FILING DATE: 30-NOV-1994
         (J) PUBLICATION DATE: 08-JUN-1995

(xi) SEQUENCE DESCRIPTION:   SEQ ID NO: 9:

CATCTGCCAT TCCCACTCTA                                                      20

(2) INFORMATION FOR SEQ ID NO: 10:

(i) SEQUENCE CHARACTERISTICS:
         (A) LENGTH: 24 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to mammalian DNA
             methyl transferase

```
    (x) PUBLICATION INFORMATION:
        (H) DOCUMENT NUMBER: WO 95/15378 (SEQ ID NO:2)
        (I) FILING DATE: 30-NOV-1994
        (J) PUBLICATION DATE: 08-JUN-1995

(xi) SEQUENCE DESCRIPTION: SEQ ID NO: 10:

TTGGCATCTG CCATTCCCAC TCTA                                          24

(2) INFORMATION FOR SEQ ID NO: 11:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
        (H) DOCUMENT NUMBER: WO 95/04142 (SEQ ID NO:1)
        (I) FILING DATE: 26-JUL-1994
        (J) PUBLICATION DATE: 09-FEB-1995

(xi) SEQUENCE DESCRIPTION: SEQ ID NO: 11:

CATGGTTTCG GAGGGCGTC                                                19

(2) INFORMATION FOR SEQ ID NO: 12:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
        (A) AUTHORS: Robinson, G.S., et al.
        (B) TITLE: Oligodeoxynucleotides inhibit retinal
            neovascularization in a murine model of proliferative
            retinopathy (SEQ ID NO: M3)
        (C) JOURNAL: The Proceedings of the National Academy of
            Sciences (U.S.A.)
        (D) VOLUME: 93
        (F) PAGES: 4851-4856
        (G) DATE: MAY-1996

(xi) SEQUENCE DESCRIPTION: SEQ ID NO: 12:

TCGCGCTCCC TCTCTCCGGC                                               20

(2) INFORMATION FOR SEQ ID NO: 13:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
```

```
        (H) DOCUMENT NUMBER: WO 95/04142 (SEQ ID NO: 4)
        (I) FILING DATE: 26-JUL-1994
        (J) PUBLICATION DATE: 09-FEB-1995

(xi) SEQUENCE DESCRIPTION: SEQ ID NO: 13:

CACCCAAGAG AGCAGAAAGT                                            20

(2) INFORMATION FOR SEQ ID NO: 14:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
        (A) AUTHORS: Nomura, M., et al.
        (B) TITLE: Possible Participation of Autocrine and Paracrine
            Vascular Endothelial Growth factors in Hypoxia-induced
            Proliferation of Endothelial Cells and Pericytes
        (C) JOURNAL: The Journal of Biological Chemistry
        (D) VOLUME: 270
        (E) ISSUE: 47
        (F) PAGES: 28316-28324
        (G) DATE: 24-NOV-1995

(xi) SEQUENCE DESCRIPTION: SEQ ID NO: 14:

CCCAAGACAG CAGAAAGTTC AT                                         22

(2) INFORMATION FOR SEQ ID NO: 15:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
        (H) DOCUMENT NUMBER: WO 95/04142 (SEQ ID NO: 5)
        (I) FILING DATE: 26-JUL-1994
        (J) PUBLICATION DATE: 09-FEB-1995

(xi) SEQUENCE DESCRIPTION: SEQ ID NO: 15:

TCGTGGGTGC AGCCTGGGAC                                            20

(2) INFORMATION FOR SEQ ID NO: 16:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
        (H) DOCUMENT NUMBER: WO 95/04142 (SEQ ID NO:11)
```

-continued (I) FILING DATE: 26-JUL-1994
   (J) PUBLICATION DATE: 09-FEB-1995

(xi) SEQUENCE DESCRIPTION: SEQ ID NO: 16:

CTGCCCGGCT CACCGCCTCG G               21

(2) INFORMATION FOR SEQ ID NO: 17:

(i) SEQUENCE CHARACTERISTICS:
   (A) LENGTH: 19 base pairs
   (B) TYPE: Nucleic Acid
   (C) STRANDEDNESS: Single
   (D) TOPOLOGY: Linear (iv) ANTI-SENSE: Yes (ix) FEATURE:
   (D) OTHER INFORMATION: Antisense to Vascular
    Endothelial Growth factor (VEGF)

(x) PUBLICATION INFORMATION:
   (H) DOCUMENT NUMBER: WO 95/04142 (SEQ ID NO: 12)
   (I) FILING DATE: 26-JUL-1994
   (J) PUBLICATION DATE: 09-FEB-1995

(xi) SEQUENCE DESCRIPTION: SEQ ID NO: 17:

CATGGTTTCG GAGGCCCGA                19

(2) INFORMATION FOR SEQ ID NO: 18:

(i) SEQUENCE CHARACTERISTICS:
   (A) LENGTH: 20 base pairs
   (B) TYPE: Nucleic Acid
   (C) STRANDEDNESS: Single
   (D) TOPOLOGY: Linear (iv) ANTI-SENSE: Yes (ix) FEATURE:
   (D) OTHER INFORMATION: Antisense to Vascular
    Endothelial Growth factor (VEGF)

(x) PUBLICATION INFORMATION:
   (H) DOCUMENT NUMBER: WO 95/04142 (SEQ ID NO: 13)
   (I) FILING DATE: 26-JUL-1994
   (J) PUBLICATION DATE: 09-FEB-1995

(xi) SEQUENCE DESCRIPTION: SEQ ID NO: 18:

CACCCAAGAC AGCAGAAAGT               20

(2) INFORMATION FOR SEQ ID NO: 19:

(i) SEQUENCE CHARACTERISTICS:
   (A) LENGTH: 20 base pairs
   (B) TYPE: Nucleic Acid
   (C) STRANDEDNESS: Single
   (D) TOPOLOGY: Linear (iv) ANTI-SENSE: Yes (ix) FEATURE:
   (D) OTHER INFORMATION: Antisense to Vascular
    Endothelial Growth factor (VEGF)

(x) PUBLICATION INFORMATION:
   (H) DOCUMENT NUMBER: WO 95/04142 (SEQ ID NO:17)
   (I) FILING DATE: 26-JUL-1994
   (J) PUBLICATION DATE: 09-FEB-1995

(xi) SEQUENCE DESCRIPTION: SEQ ID NO: 19:

CCATGGGTGC AGCCTGGGAC               20

```
(2) INFORMATION FOR SEQ ID NO: 20:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF)

(x) PUBLICATION INFORMATION:
        (H) DOCUMENT NUMBER: WO 95/04142 (SEQ ID NO: 17)
        (I) FILING DATE: 26-JUL-1994
        (J) PUBLICATION DATE: 09-FEB-1995

(xi) SEQUENCE DESCRIPTION:  SEQ ID NO: 20:

CCATGGGTGC AGCCTGGGAC                                            20

(2) INFORMATION FOR SEQ ID NO: 21:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Vascular
            Endothelial Growth factor (VEGF); a.k.a. "Vm"

(x) PUBLICATION INFORMATION:
        (A) AUTHORS: Robinson, G.S., et al.
        (B) TITLE: Oligodeoxynucleotides inhibit retinal
            neovascularization in a murine model of proliferative
            retinopathy
        (C) JOURNAL: The Proceedings of the National Academy
            of Sciences (U.S.A.)
        (D) VOLUME: 93
        (F) PAGES: 4851-4856
        (G) DATE: MAY-1996

(x) PUBLICATION INFORMATION:
        (H) DOCUMENT NUMBER: WO 95/04142 (SEQ ID NO:2)
        (I) FILING DATE: 26-JUL-1994
        (J) PUBLICATION DATE: 09-FEB-1995

(xi) SEQUENCE DESCRIPTION:  SEQ ID NO: 21:

CAGCCTGGCT CACCGCCTTG G                                          21

(2) INFORMATION FOR SEQ ID NO: 22:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 1)
        (I) FILING DATE: 20-SEP-1994
        (J) PUBLICATION DATE: 30-MAR-1995

(xi) SEQUENCE DESCRIPTION:  SEQ ID NO: 22:
```

CCCTTCCTAC CGCGTGCGAC                                                    20

(2) INFORMATION FOR SEQ ID NO: 23:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 3)
        (I) FILING DATE: 20-SEP-1994
        (J) PUBLICATION DATE: 30-MAR-1995

(xi) SEQUENCE DESCRIPTION:  SEQ ID NO: 23:

CCTCCGACCC ATCCACGTAG                                                    20

(2) INFORMATION FOR SEQ ID NO: 24:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 5)
        (I) FILING DATE: 20-SEP-1994
        (J) PUBLICATION DATE: 30-MAR-1995

(xi) SEQUENCE DESCRIPTION:  SEQ ID NO: 24:

GTTGACGTCC TACGGAAACA                                                    20

(2) INFORMATION FOR SEQ ID NO: 25:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 8)
        (I) FILING DATE: 20-SEP-1994
        (J) PUBLICATION DATE: 30-MAR-1995

(xi) SEQUENCE DESCRIPTION:  SEQ ID NO: 25:

CGCGTGCGAC CCTCTTG                                                       17

(2) INFORMATION FOR SEQ ID NO: 26:

(i) SEQUENCE CHARACTERISTICS:
        (A) LENGTH: 17 base pairs
        (B) TYPE: Nucleic Acid
        (C) STRANDEDNESS: Single (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 9)
        (I) FILING DATE: 20-SEP-1994
        (J) PUBLICATION DATE: 30-MAR-1995

(xi) SEQUENCE DESCRIPTION:  SEQ ID NO: 26:

TCCTACCGCG TGCGACC                                                17

(2) INFORMATION FOR SEQ ID NO: 27:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 10)
        (I) FILING DATE: 20-SEP-1994
        (J) PUBLICATION DATE: 30-MAR-1995

(xi) SEQUENCE DESCRIPTION:  SEQ ID NO: 27:

TCCTACCGCG TGCGACC                                                17

(2) INFORMATION FOR SEQ ID NO: 28:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 11)
        (I) FILING DATE: 20-SEP-1994
        (J) PUBLICATION DATE: 30-MAR-1995

(xi) SEQUENCE DESCRIPTION:  SEQ ID NO: 28:

CCTTCCTACC GCGTGCG                                                17

(2) INFORMATION FOR SEQ ID NO: 29:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 12)
        (I) FILING DATE: 20-SEP-1994

-continued (J) PUBLICATION DATE: 30-MAR-1995

(xi) SEQUENCE DESCRIPTION: SEQ ID NO: 29:

GACCCTTCCT ACCGCGT                           17

(2) INFORMATION FOR SEQ ID NO: 30:

(i) SEQUENCE CHARACTERISTICS:
    (A) LENGTH: 17 base pairs
    (C) STRANDEDNESS: Single
    (D) TOPOLOGY: Linear (iv) ANTI-SENSE: Yes (ix) FEATURE:
    (D) OTHER INFORMATION: Antisense to bcl-2 mRNA (x) PUBLICATION INFORMATION:
    (H) DOCUMENT NUMBER: WO 95/08350 (SEQ ID NO: 13)
    (I) FILING DATE: 20-SEP-1994
    (J) PUBLICATION DATE: 30-MAR-1995

(xi) SEQUENCE DESCRIPTION: SEQ ID NO: 30:

GGAGACCCTT CCTACCG                           17

(2) INFORMATION FOR SEQ ID NO: 31:

(i) SEQUENCE CHARACTERISTICS:
    (A) LENGTH: 15 base pairs
    (B) TYPE: Nucleic Acid
    (C) STRANDEDNESS: Single
    (D) TOPOLOGY: Linear (iv) ANTI-SENSE: Yes (ix) FEATURE:
    (D) OTHER INFORMATION: Antisense to bcl-2 mRNA (x) PUBLICATION INFORMATION:
    (H) DOCUMENT NUMBER: WO 95/08350 (SEQ ID NO: 14)
    (I) FILING DATE: 20-SEP-1994
    (J) PUBLICATION DATE: 30-MAR-1995

(xi) SEQUENCE DESCRIPTION: SEQ ID NO: 31:

GCGGCGGCAG CGCGG                            15

(2) INFORMATION FOR SEQ ID NO: 32:

(i) SEQUENCE CHARACTERISTICS:
    (A) LENGTH: 15 base pairs
    (B) TYPE: Nucleic Acid
    (C) STRANDEDNESS: Single
    (D) TOPOLOGY: Linear (iv) ANTI-SENSE: Yes (ix) FEATURE:
    (D) OTHER INFORMATION: Antisense to bcl-2 mRNA (x) PUBLICATION INFORMATION:
    (H) DOCUMENT NUMBER: WO 95/08350 (SEQ ID NO: 15)
    (I) FILING DATE: 20-SEP-1994
    (J) PUBLICATION DATE: 30-MAR-1995

(xi) SEQUENCE DESCRIPTION: SEQ ID NO: 32:

CGGCGGGGCG ACGGA                            15

(2) INFORMATION FOR SEQ ID NO: 33:

(i) SEQUENCE CHARACTERISTICS:
    (A) LENGTH: 16 base pairs

```
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA (x) PUBLICATION INFORMATION:
        (H) DOCUMENT NUMBER: WO 95/08350 (SEQ ID NO: 16)
        (I) FILING DATE: 20-SEP-1994
        (J) PUBLICATION DATE: 30-MAR-1995

(xi) SEQUENCE DESCRIPTION:  SEQ ID NO: 33:

CGGGAGCGCG GCGGGC                                                     16

(2) INFORMATION FOR SEQ ID NO: 34:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl-2 mRNA; a.k.a. "BCL-2"

(x) PUBLICATION INFORMATION:
        (H) DOCUMENT NUMBER: WO 95/08350 (SEQ ID NO:17)
        (I) FILING DATE: 20-SEP-1994
        (J) PUBLICATION DATE: 30-MAR-1995

(xi) SEQUENCE DESCRIPTION:  SEQ ID NO: 34:

TCTCCCAGCG TGCGCCAT                                                   18

(2) INFORMATION FOR SEQ ID NO: 35:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bcl/abl mRNA (x) PUBLICATION INFORMATION:
        (H) DOCUMENT NUMBER: WO 92/02641
        (I) FILING DATE: 09-AUG-1991
        (J) PUBLICATION DATE: 20-FEB-1992

(xi) SEQUENCE DESCRIPTION:  SEQ ID NO: 35:

GGCGTTTTGA ACTCTGCTT                                                  19

(2) INFORMATION FOR SEQ ID NO: 36:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to several isoforms of PKC;
            a.k.a. "oligoanti-PKCa"
```

(x) PUBLICATION INFORMATION:
    (A) AUTHORS: Shih, M., et al.
    (B) TITLE: Oligodeoxynucleotides antisense to mRNA encoding
        protein kinase A, protein kinase C and b-adrenergic
        receptor kinase reveal distinctive cell-type-specific
        roles in agonist-induced des
    (C) JOURNAL: The Proceedings of the National Academy of
        Sciences (U.S.A.)
    (D) VOLUME: 91
    (F) PAGES: 12193-12197
    (G) DATE: 06-DEC-1994

(xi) SEQUENCE DESCRIPTION: SEQ ID NO: 36:

AAGGTGGGCT GCTTGAAGAA                                               20

(2) INFORMATION FOR SEQ ID NO: 37:

(i) SEQUENCE CHARACTERISTICS:
        (A) LENGTH: 15 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to z-Protein Kinase C gene (x) PUBLICATION INFORMATION:
        (H) DOCUMENT NUMBER: WO 93/20101 (SEQ ID NO:14)
        (I) FILING DATE: 02-APR-1993
        (J) PUBLICATION DATE: 14-OCT-199

(xi) SEQUENCE DESCRIPTION: SEQ ID NO: 37:

GGTCCTGCTG GGCAT                                                    15

(2) INFORMATION FOR SEQ ID NO: 38:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to a-Protein Kinase C gene;
            a.k.a. "ISIS 3521"

(x) PUBLICATION INFORMATION:
        (H) DOCUMENT NUMBER: WO 95/02069 (SEQ ID NO:2)
        (I) FILING DATE: 08-JUL-1994
        (J) PUBLICATION DATE: 19-JAN-1995

(xi) SEQUENCE DESCRIPTION: SEQ ID NO: 38:

GTTCTCGCTG GTGAGTTTCA                                               20

(2) INFORMATION FOR SEQ ID NO: 39:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes (x) PUBLICATION INFORMATION:
        (H) DOCUMENT NUMBER: WO 97/11171 (SEQ ID NO:1)
        (I) FILING DATE: 19-SEP-1996
        (J) PUBLICATION DATE: 27-MAR-1997

-continued (xi) SEQUENCE DESCRIPTION: SEQ ID NO: 39:

GCGTGCCTCC TCACTGGC                                                                 18

(2) INFORMATION FOR SEQ ID NO: 40:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes (x) PUBLICATION INFORMATION:
        (H) DOCUMENT NUMBER: WO 97/11171 (SEQ ID NO:4)
        (I) FILING DATE: 19-SEP-1996
        (J) PUBLICATION DATE: 27-MAR-1997

(xi) SEQUENCE DESCRIPTION: SEQ ID NO: 40:

GCGUGCCTCC TCACUGGC                                                                 18

(2) INFORMATION FOR SEQ ID NO: 41:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes (x) PUBLICATION INFORMATION:
        (H) DOCUMENT NUMBER: WO 97/11171 (SEQ ID NO:6)
        (I) FILING DATE: 19-SEP-1996
        (J) PUBLICATION DATE: 27-MAR-1997

(xi) SEQUENCE DESCRIPTION: SEQ ID NO: 41:

GCGTGCCUCC UCACTGGC                                                                 18

(2) INFORMATION FOR SEQ ID NO: 42:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to bARK1 and bARK2; a.k.a. as
            "oligoanti-bARK2"

(x) PUBLICATION INFORMATION:
        (A) AUTHORS: Shih, M., et al.
        (B) TITLE: Oligodeoxynucleotides antisense to mRNA encoding
            protein kinase A, protein kinase C and b-adrenergic
            receptor kinase reveal distinctive cell-type-specific
            roles in agonist-induced des
        (C) JOURNAL: The Proceedings of the National Academy of
            Sciences (U.S.A.)
        (D) VOLUME: 91
        (F) PAGES: 12193-12197
        (G) DATE: 06-DEC-1994

(xi) SEQUENCE DESCRIPTION: SEQ ID NO: 42:

ACCGCCTCCA GGTCCGCCAT                                                               20

(2) INFORMATION FOR SEQ ID NO: 43:

(i) SEQUENCE CHARACTERISTICS:

```
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Ha-ras Gene;
            a.k.a. "ISIS 2503"

(x) PUBLICATION INFORMATION:
        (H) DOCUMENT NUMBER: US 5576208 (SEQ ID NO:2)
        (I) FILING DATE: 26-AUG-1994
        (J) PUBLICATION DATE: 19-NOV-1996

(xi) SEQUENCE DESCRIPTION:  SEQ ID NO: 43:

TCCGTCATCG CTCCTCAGGG                                                   20

(2) INFORMATION FOR SEQ ID NO: 44:

(i) SEQUENCE CHARACTERISTICS:
        (A) LENGTH: 22 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Multi-drug
            Resistance-1 (MDR-1) gene (x) PUBLICATION INFORMATION:
        (H) DOCUMENT NUMBER: WO 96/02556 (SEQ ID NO:1)
        (I) FILING DATE: 18-JUL-1995
        (J) PUBLICATION DATE: 01-FEB-1996

(xi) SEQUENCE DESCRIPTION:  SEQ ID NO: 44:

TGTGCTCTTC CCACAGCCAC TG                                                22

(2) INFORMATION FOR SEQ ID NO: 45:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Multi-drug
            Resistance-1 (MDR-1) gene (x) PUBLICATION INFORMATION:
        (H) DOCUMENT NUMBER: WO 96/02556 (SEQ ID NO:2)
        (I) FILING DATE: 18-JUL-1995
        (J) PUBLICATION DATE: 01-FEB-1996

(xi) SEQUENCE DESCRIPTION:  SEQ ID NO: 45:

TGTGCTCTTC CCACAGCCAC                                                   20

(2) INFORMATION FOR SEQ ID NO: 46:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes
```

```
    (ix) FEATURE:
         (D) OTHER INFORMATION: Antisense to Multi-drug
             Resistance-1 (MDR-1) gene (x) PUBLICATION INFORMATION:
         (H) DOCUMENT NUMBER: WO 96/02556 (SEQ ID NO:3)
         (I) FILING DATE: 18-JUL-1995
         (J) PUBLICATION DATE: 01-FEB-1996

(xi) SEQUENCE DESCRIPTION:  SEQ ID NO: 46:

GTGCTCTTCC CACAGCCACT                                              20

(2) INFORMATION FOR SEQ ID NO: 47:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to Multi-drug
             Resistance-1 (MDR-1) gene (x) PUBLICATION INFORMATION:
         (H) DOCUMENT NUMBER: WO 96/02556 (SEQ ID NO:4)
         (I) FILING DATE: 18-JUL-1995
         (J) PUBLICATION DATE: 01-FEB-1996

(xi) SEQUENCE DESCRIPTION:  SEQ ID NO: 47:

TGCTCTTCCC ACAGCCACTG                                              20

(2) INFORMATION FOR SEQ ID NO: 48:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to multidrug resistance-
             associated protein (MRP) gene; a.k.a. "ISIS 7597"

(x) PUBLICATION INFORMATION:
         (H) DOCUMENT NUMBER: US 5510239 (SEQ ID NO:8)
         (I) FILING DATE: 18-OCT-1993
         (J) PUBLICATION DATE: 23-APR-1996

(xi) SEQUENCE DESCRIPTION:  SEQ ID NO: 48:

TGCTGTTCGT GCCCCCGCCG                                              20

(2) INFORMATION FOR SEQ ID NO: 49:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to A-raf gene; a.k.a. "ISIS
             9069"

(x) PUBLICATION INFORMATION:
         (H) DOCUMENT NUMBER: US 5563255 (SEQ ID NO:37)
         (I) FILING DATE: 31-MAY-1994
```

-continued (J) PUBLICATION DATE: 08-OCT-1996

(xi) SEQUENCE DESCRIPTION: SEQ ID NO: 49:

CTAAGGCACA AGGCGGGCTG                     20

(2) INFORMATION FOR SEQ ID NO: 50:

(i) SEQUENCE CHARACTERISTICS:
    (A) LENGTH: 20 base pairs
    (B) TYPE: Nucleic Acid
    (C) STRANDEDNESS: Single
    (D) TOPOLOGY: Linear (iv) ANTI-SENSE: Yes (ix) FEATURE:
    (D) OTHER INFORMATION: Antisense to c-raf kinase
      Gene; a.k.a. "ISIS 5132"

(x) PUBLICATION INFORMATION:
    (H) DOCUMENT NUMBER: US 5563255 (SEQ ID NO:8)
    (I) FILING DATE: 05-31-1994
    (J) PUBLICATION DATE: 08-OCT-1996

(xi) SEQUENCE DESCRIPTION: SEQ ID NO: 50:

TCCCGCCTGT GACATGCATT                     20

(2) INFORMATION FOR SEQ ID NO: 51:

(i) SEQUENCE CHARACTERISTICS:
    (A) LENGTH: 25 base pairs
    (B) TYPE: Nucleic Acid
    (C) STRANDEDNESS: Single
    (D) TOPOLOGY: Linear (iv) ANTI-SENSE: Yes (ix) FEATURE:
    (D) OTHER INFORMATION: Antisense to beta/A4 peptide (x) PUBLICATION INFORMATION:
    (H) DOCUMENT NUMBER: WO 95/09236 (SEQ ID NO:1)
    (I) FILING DATE: 28-SEP-1994
    (J) PUBLICATION DATE: 06-APR-1995

(xi) SEQUENCE DESCRIPTION: SEQ ID NO: 51:

CCTCTCTGTT TAAAACTTTA TCCAT                 25

(2) INFORMATION FOR SEQ ID NO: 52:

(i) SEQUENCE CHARACTERISTICS:
    (A) LENGTH: 21 base pairs
    (B) TYPE: Nucleic Acid
    (C) STRANDEDNESS: Single
    (D) TOPOLOGY: Linear (iv) ANTI-SENSE: Yes (ix) FEATURE:
    (D) OTHER INFORMATION: Antisense to beta/A4 peptide (x) PUBLICATION INFORMATION:
    (H) DOCUMENT NUMBER: WO 95/09236 (SEQ ID NO:2)
    (I) FILING DATE: 28-SEP-1994
    (J) PUBLICATION DATE: 06-APR-1995

(xi) SEQUENCE DESCRIPTION: SEQ ID NO: 52:

TTCATATCCT GAGTCATGTC G                    21

(2) INFORMATION FOR SEQ ID NO: 53:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:3)
        (I) FILING DATE: 28-SEP-1994
        (J) PUBLICATION DATE: 06-APR-1995

(xi) SEQUENCE DESCRIPTION:  SEQ ID NO: 53:

GTCCCAGCGC TACGACGGGC CAAA                                              24

(2) INFORMATION FOR SEQ ID NO: 54:

(i) SEQUENCE CHARACTERISTICS:
        (A) LENGTH: 13 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:4)
        (I) FILING DATE: 28-SEP-1994
        (J) PUBLICATION DATE: 06-APR-1995

(xi) SEQUENCE DESCRIPTION:  SEQ ID NO: 54:

GTCCCAGCGC TAC                                                          13

(2) INFORMATION FOR SEQ ID NO: 55:

(i) SEQUENCE CHARACTERISTICS:
        (A) LENGTH: 14 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:5)
        (I) FILING DATE: 28-SEP-1994
        (J) PUBLICATION DATE: 06-APR-1995

(xi) SEQUENCE DESCRIPTION:  SEQ ID NO: 55:

TACGACGGGC CAAA                                                         14

(2) INFORMATION FOR SEQ ID NO: 56:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide

```
    (x) PUBLICATION INFORMATION:
        (H) DOCUMENT NUMBER: WO 95/09236 (SEQ ID NO:6)
        (I) FILING DATE: 28-SEP-1994
        (J) PUBLICATION DATE: 06-APR-1995

(xi) SEQUENCE DESCRIPTION:  SEQ ID NO: 56:

GTCCCAGCGC TACGACGGGC C                                              21

(2) INFORMATION FOR SEQ ID NO: 57:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:7)
        (I) FILING DATE: 28-SEP-1994
        (J) PUBLICATION DATE: 06-APR-1995

(xi) SEQUENCE DESCRIPTION:  SEQ ID NO: 57:

GTCCCAGCGC TACGACGG                                                  18

(2) INFORMATION FOR SEQ ID NO: 58:

(i) SEQUENCE CHARACTERISTICS:
        (A) LENGTH: 15 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:8)
        (I) FILING DATE: 28-SEP-1994
        (J) PUBLICATION DATE: 06-APR-1995

(xi) SEQUENCE DESCRIPTION:  SEQ ID NO: 58:

GTCCCAGCGC TACGA                                                     15

(2) INFORMATION FOR SEQ ID NO: 59:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:9)
        (I) FILING DATE: 28-SEP-1994
        (J) PUBLICATION DATE: 06-APR-1995

(xi) SEQUENCE DESCRIPTION:  SEQ ID NO: 59:

CCAGCGCTAC GACGGGCCAA A                                              21
```

```
(2) INFORMATION FOR SEQ ID NO: 60:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:10)
        (I) FILING DATE: 28-SEP-1994
        (J) PUBLICATION DATE: 06-APR-1995

(xi) SEQUENCE DESCRIPTION:  SEQ ID NO: 60:

GCGCTACGAC GGGCCAAA                                              18

(2) INFORMATION FOR SEQ ID NO: 61:

(i) SEQUENCE CHARACTERISTICS:
        (A) LENGTH: 15 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:11)
        (I) FILING DATE: 28-SEP-1994
        (J) PUBLICATION DATE: 06-APR-1995

(xi) SEQUENCE DESCRIPTION:  SEQ ID NO: 61:

CTACGACGGG CCAAA                                                 15

(2) INFORMATION FOR SEQ ID NO: 62:

(i) SEQUENCE CHARACTERISTICS:
        (A) LENGTH: 24 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to beta/A4 peptide (x) PUBLICATION INFORMATION:
        (H) DOCUMENT NUMBER: WO 95/09236 (SEQ ID NO:15)
        (I) FILING DATE: 28-SEP-1994
        (J) PUBLICATION DATE: 06-APR-1995

(xi) SEQUENCE DESCRIPTION:  SEQ ID NO: 62:

AAACCGGGCA GCATCGCGAC CCTG                                       24

(2) INFORMATION FOR SEQ ID NO: 63:

(i) SEQUENCE CHARACTERISTICS:
        (A) LENGTH: 18 base pairs
        (B) TYPE: Nucleic Acid
        (C) STRANDEDNESS: Single
        (D) TOPOLOGY: Linear (iv) ANTI-SENSE: Yes
```

(ix) FEATURE:
            (D) OTHER INFORMATION: Antisense to beta-globin; a.k.a. "5'ss"

(x) PUBLICATION INFORMATION:
            (A) AUTHORS: Sierakowska, H., et al.
            (B) TITLE: Repair of thalassemic human b-globin in mammalian
                cells by antisense oligonucleotides
            (C) JOURNAL: The Proceedings of the National Academy of
                Sciences (U.S.A.)
            (D) VOLUME: 93
            (F) PAGES: 12840-12844
            (G) DATE: 12-NOV-1996

(xi) SEQUENCE DESCRIPTION: SEQ ID NO: 63:

GCUAUUACCU UAACCCAG                                                    18

(2) INFORMATION FOR SEQ ID NO: 64:

(i) SEQUENCE CHARACTERISTICS:
            (A) LENGTH: 17 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to beta-globin; a.k.a. "3'ss"

(x) PUBLICATION INFORMATION:
            (A) AUTHORS: Sierakowska, H., et al.
            (B) TITLE: Repair of thalassemic human B-gobin in mammalian
                cells by antisense oligonucleotides
            (C) JOURNAL: The Proceedings of the National Academy of
                Sciences (U.S.A.)
            (D) VOLUME: 93
            (F) PAGES: 12840-12844
            (G) DATE: 12-NOV-1996

(xi) SEQUENCE DESCRIPTION: SEQ ID NO: 64:

CAUUAUUGCC CUGAAAG                                                     17

(2) INFORMATION FOR SEQ ID NO: 65:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to malarial agents; a.k.a.
                "PSI"

(x) PUBLICATION INFORMATION:
            (H) DOCUMENT NUMBER: WO 93/13740
            (I) FILING DATE: 31-DEC-1991
            (J) PUBLICATION DATE: 22-JUL-1993

(xi) SEQUENCE DESCRIPTION: SEQ ID NO: 65:

TAAAAAGAAT ATGATCTTCA T                                                21

(2) INFORMATION FOR SEQ ID NO: 66:

(i) SEQUENCE CHARACTERISTICS:
            (A) LENGTH: 18 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to malarial agents; a.k.a.
                "PSII"

(x) PUBLICATION INFORMATION:
            (H) DOCUMENT NUMBER: WO 93/13740 (SEQ ID NO: PSII)
            (I) FILING DATE: 31-DEC-1991
            (J) PUBLICATION DATE: 22-JUL-1993

(xi) SEQUENCE DESCRIPTION:  SEQ ID NO: 66:

AGCAACTGAG CCACCTGA                                                          18

(2) INFORMATION FOR SEQ ID NO: 67:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to malarial agents; a.k.a.
                "PSIII"

(x) PUBLICATION INFORMATION:
            (H) DOCUMENT NUMBER: WO 93/13740
            (I) FILING DATE: 31-DEC-1991
            (J) PUBLICATION DATE: 22-JUL-1993

(xi) SEQUENCE DESCRIPTION:  SEQ ID NO: 67:

GTCGCAGACT TGTTCCATCA T                                                      21

(2) INFORMATION FOR SEQ ID NO: 68:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to malarial agents; a.k.a.
                "RI"

(x) PUBLICATION INFORMATION:
            (H) DOCUMENT NUMBER: WO 93/13740
            (I) FILING DATE: 31-DEC-1991
            (J) PUBLICATION DATE: 22-JUL-1993

(xi) SEQUENCE DESCRIPTION:  SEQ ID NO: 68:

CTTGGCAGCT GCGCGTGACA T                                                      21

(2) INFORMATION FOR SEQ ID NO: 69:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to scistosome worms (x) PUBLICATION INFORMATION:
            (H) DOCUMENT NUMBER: WO 95/33759 (SEQ ID NO:1)

```
        (I) FILING DATE: 30-MAY-1995
        (J) PUBLICATION DATE: 14-DEC-1995

(xi) SEQUENCE DESCRIPTION:  SEQ ID NO: 69:

GCCATAGGGG GCAGGGAAGG C                                                 21

(2) INFORMATION FOR SEQ ID NO: 70:

(i) SEQUENCE CHARACTERISTICS:
        (A) LENGTH: 12 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HTLV-III (x) PUBLICATION INFORMATION:
        (H) DOCUMENT NUMBER: WO 87/07300 (SEQ ID NO:A)
        (I) FILING DATE: 22-MAY-1987
        (J) PUBLICATION DATE: 03-DEC-1987

(xi) SEQUENCE DESCRIPTION:  SEQ ID NO: 70:

CTGCTAGAGA TT                                                           12

(2) INFORMATION FOR SEQ ID NO: 71:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HTLV-III (x) PUBLICATION INFORMATION:
        (H) DOCUMENT NUMBER: WO 87/07300 (SEQ ID NO:B)
        (I) FILING DATE: 22-MAY-1987
        (J) PUBLICATION DATE: 03-DEC-1987

(xi) SEQUENCE DESCRIPTION:  SEQ ID NO: 71:

CTGCTAGAGA TTTTCCACAC                                                   20

(2) INFORMATION FOR SEQ ID NO: 72:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HTLV-III (x) PUBLICATION INFORMATION:
        (H) DOCUMENT NUMBER: WO 87/07300 (SEQ ID NO:C)
        (I) FILING DATE: 22-MAY-1987
        (J) PUBLICATION DATE: 03-DEC-1987

(xi) SEQUENCE DESCRIPTION:  SEQ ID NO: 72:

TTCAAGTCCC TGTTCGGGCG CCAAA                                             25

(2) INFORMATION FOR SEQ ID NO: 73:
```

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HTLV-III (x) PUBLICATION INFORMATION:
            (H) DOCUMENT NUMBER: WO 87/07300 (SEQ ID NO:D)
            (I) FILING DATE: 22-MAY-1987
            (J) PUBLICATION DATE: 03-DEC-1987

(xi) SEQUENCE DESCRIPTION:   SEQ ID NO: 73:

GCGTACTCAC CAGTCGCCGC                                                        20

(2) INFORMATION FOR SEQ ID NO: 74:

(i) SEQUENCE CHARACTERISTICS:
            (A) LENGTH: 14 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HTLV-III (x) PUBLICATION INFORMATION:
            (H) DOCUMENT NUMBER: WO 87/07300 (SEQ ID NO:E)
            (I) FILING DATE: 22-MAY-1987
            (J) PUBLICATION DATE: 03-DEC-1987

(xi) SEQUENCE DESCRIPTION:   SEQ ID NO: 74:

CTGCTAGAGA TTAA                                                              14

(2) INFORMATION FOR SEQ ID NO: 75:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HTLV-III (x) PUBLICATION INFORMATION:
            (H) DOCUMENT NUMBER: WO 87/07300 (SEQ ID NO:F)
            (I) FILING DATE: 22-MAY-1987
            (J) PUBLICATION DATE: 03-DEC-1987

(xi) SEQUENCE DESCRIPTION:   SEQ ID NO: 75:

ACACCCAATT CTGAAAATGG                                                        20

(2) INFORMATION FOR SEQ ID NO: 76:

(i) SEQUENCE CHARACTERISTICS:
            (A) LENGTH: 25 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV-1

```
    (x) PUBLICATION INFORMATION:
        (A) AUTHORS: Agrawal, Sudhir
                     Tang, Jin Yan
        (B) TITLE: GEM 91-An Antisense Oligonucleotide
            Phosphorothioate as a Therapeutic Agent for AIDS
        (C) JOURNAL: Antisense Research and Development
        (D) VOLUME: 2
        (E) ISSUE: 6
        (F) PAGES: 261-266
        (G) DATE: Winter-1992

(x) PUBLICATION INFORMATION:
        (H) DOCUMENT NUMBER: WO 94/08004 (SEQ ID NO:1)
        (I) FILING DATE: 04-OCT-1993
        (J) PUBLICATION DATE: 14-APR-1994

(xi) SEQUENCE DESCRIPTION:  SEQ ID NO: 76:

CTCTCGCACC CATCTCTCTC CTTCT                                          25

(2) INFORMATION FOR SEQ ID NO: 77:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:2)
        (I) FILING DATE: 04-OCT-1993
        (J) PUBLICATION DATE: 14-APR-1994

(xi) SEQUENCE DESCRIPTION:  SEQ ID NO: 77:

CTCTCGCACC CATCTCTCTC CTTCTA                                         26

(2) INFORMATION FOR SEQ ID NO: 78:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:3)
        (I) FILING DATE: 04-OCT-1993
        (J) PUBLICATION DATE: 14-APR-1994

(xi) SEQUENCE DESCRIPTION:  SEQ ID NO: 78:

GCTCTCGCAC CCATCTCTCT CCTTCT                                         26

(2) INFORMATION FOR SEQ ID NO: 79:

(i) SEQUENCE CHARACTERISTICS:
        (A) LENGTH: 27 base pairs
        (B) TYPE: Nucleic Acid
        (C) STRANDEDNESS: Single
        (D) TOPOLOGY: Linear (iv) ANTI-SENSE: Yes
```

(ix) FEATURE:
        (D) OTHER INFORMATION: Antisense to HIV-1

(x) PUBLICATION INFORMATION:
        (H) DOCUMENT NUMBER: WO 94/08004 (SEQ ID NO:4)
        (I) FILING DATE: 04-OCT-1993
        (J) PUBLICATION DATE: 14-APR-1994

(xi) SEQUENCE DESCRIPTION: SEQ ID NO: 79:

GCTCTCGCAC CCATCTCTCT CCTTCTA                                27

(2) INFORMATION FOR SEQ ID NO: 80:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:5)
        (I) FILING DATE: 04-OCT-1993
        (J) PUBLICATION DATE: 14-APR-1994

(xi) SEQUENCE DESCRIPTION: SEQ ID NO: 80:

GCTCTCGCAC CCATCTCTCT CCTTCTAG                               28

(2) INFORMATION FOR SEQ ID NO: 81:

(i) SEQUENCE CHARACTERISTICS:
        (A) LENGTH: 28 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:6)
        (I) FILING DATE: 04-OCT-1993
        (J) PUBLICATION DATE: 14-APR-1994

(xi) SEQUENCE DESCRIPTION: SEQ ID NO: 81:

CGCTCTCGCA CCCATCTCTC TCCTTCTA                               28

(2) INFORMATION FOR SEQ ID NO: 82:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:7)
        (I) FILING DATE: 04-OCT-1993
        (J) PUBLICATION DATE: 14-APR-1994

(xi) SEQUENCE DESCRIPTION: SEQ ID NO: 82:

CGCTCTCGCA CCCATCTCTC TCCTTCTAG                             29

(2) INFORMATION FOR SEQ ID NO: 83:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:8)
        (I) FILING DATE: 04-OCT-1993
        (J) PUBLICATION DATE: 14-APR-1994

(xi) SEQUENCE DESCRIPTION:  SEQ ID NO: 83:

CGCTCTCGCA CCCATCTCTC TCCTTCTAGC                            30

(2) INFORMATION FOR SEQ ID NO: 84:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:9)
        (I) FILING DATE: 04-OCT-1993
        (J) PUBLICATION DATE: 14-APR-1994

(xi) SEQUENCE DESCRIPTION:  SEQ ID NO: 84:

ACGCTCTCGC ACCCATCTCT CTCCTTCTAG                            30

(2) INFORMATION FOR SEQ ID NO:85:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV-1

(x) PUBLICATION INFORMATION:
        (H) DOCUMENT NUMBER: WO 94/08004 (SEQ ID NO:10)
        (I) FILING DATE: 04-OCT-1993
        (J) PUBLICATION DATE: 14-APR-1994

(xi) SEQUENCE DESCRIPTION:  SEQ ID NO: 85:

CTCGCACCCA TCTCTCTCCT                                       20

(2) INFORMATION FOR SEQ ID NO: 86:

(i) SEQUENCE CHARACTERISTICS:
        (A) LENGTH: 17 base pairs
        (B) TYPE: Nucleic Acid
        (C) STRANDEDNESS: Single
        (D) TOPOLOGY: Linear (iv) ANTI-SENSE: Yes (ix) FEATURE:
             (D) OTHER INFORMATION: Antisense to HIV-1; a.k.a.
                 "AR 177"

(x) PUBLICATION INFORMATION:
             (A) AUTHORS: Bishop, J.S., et al.
             (B) TITLE: Intramolecular G-quartet Motifs Confer
                 Nuclease Resistance to a Potent Anti-HIV
                 Oligonucleotide
             (C) JOURNAL: The Journal of Biological Chemistry
             (D) VOLUME: 271
             (E) ISSUE: 10
             (F) PAGES: 5698-5703
             (G) DATE: 08-MAR-1996

(xi) SEQUENCE DESCRIPTION:  SEQ ID NO: 86:

GTGGTGGGTG GGTGGGT                                                      17

(2) INFORMATION FOR SEQ ID NO: 87:

(i) SEQUENCE CHARACTERISTICS:
             (A) LENGTH: 26 base pairs
             (B) TYPE: Nucleic Acid
             (C) STRANDEDNESS: Single
             (D) TOPOLOGY: Linear (iv) ANTI-SENSE: Yes (ix) FEATURE:
             (D) OTHER INFORMATION: Antisense to HIV (xi) SEQUENCE DESCRIPTION:  SEQ ID NO: 87:

GCCTATTCTG CTATGTCGAC ACCCAA                                            26

(2) INFORMATION FOR SEQ ID NO: 88:

(i) SEQUENCE CHARACTERISTICS:
             (A) LENGTH: 26 base pairs
             (B) TYPE: Nucleic Acid
             (C) STRANDEDNESS: Single
             (D) TOPOLOGY: Linear (iv) ANTI-SENSE: Yes (ix) FEATURE:
             (D) OTHER INFORMATION: Antisense to HIV (xi) SEQUENCE DESCRIPTION:  SEQ ID NO: 88:

CTTCGGGCCT GTCGGGTCCC CTCGGG                                            26

(2) INFORMATION FOR SEQ ID NO: 89:

(i) SEQUENCE CHARACTERISTICS:
             (A) LENGTH: 26 base pairs
             (B) TYPE: Nucleic Acid
             (C) STRANDEDNESS: Single
             (D) TOPOLOGY: Linear (iv) ANTI-SENSE: Yes (ix) FEATURE:
             (D) OTHER INFORMATION: Antisense to HIV (x) PUBLICATION INFORMATION:
             (H) DOCUMENT NUMBER: WO 95/03407
             (I) FILING DATE: 19-JUL-1994
             (J) PUBLICATION DATE: 02-FEB-1995

(xi) SEQUENCE DESCRIPTION:  SEQ ID NO: 89:

CTTCGGGCCT GTCGGGTCCC CTCGGG                                         26

(2) INFORMATION FOR SEQ ID NO: 90:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV (x) PUBLICATION INFORMATION:
        (H) DOCUMENT NUMBER: WO 96/02557 (SEQ ID NO:3)
        (I) FILING DATE: 14-JUL-1995
        (J) PUBLICATION DATE: 01-FEB-1996

(xi) SEQUENCE DESCRIPTION: SEQ ID NO: 90:

GCTGGTGATC CTTTCCATCC CTGTGG                                         26

(2) INFORMATION FOR SEQ ID NO: 91:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV (x) PUBLICATION INFORMATION:
        (H) DOCUMENT NUMBER: WO 96/02557 (SEQ ID NO:5)
        (I) FILING DATE: 14-JUL-1995
        (J) PUBLICATION DATE: 01-FEB-1996

(xi) SEQUENCE DESCRIPTION: SEQ ID NO: 91:

CTACTACTCC TTGACTTTGG GGATTG                                         26

(2) INFORMATION FOR SEQ ID NO: 92:

(i) SEQUENCE CHARACTERISTICS:
        (A) LENGTH: 29 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV (x) PUBLICATION INFORMATION:
        (H) DOCUMENT NUMBER: WO 96/02557 (SEQ ID NO:6)
        (I) FILING DATE: 14-JUL-1995
        (J) PUBLICATION DATE: 01-FEB-1996

(xi) SEQUENCE DESCRIPTION: SEQ ID NO: 92:

CCTCTGTTAG TAACATATCC TGCTTTTCC                                      29

(2) INFORMATION FOR SEQ ID NO: 93:

(i) SEQUENCE CHARACTERISTICS:
        (A) LENGTH: 26 base pairs
        (B) TYPE: Nucleic Acid
        (C) STRANDEDNESS: Single (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 96/02557 (SEQ ID NO:8)
            (I) FILING DATE: 14-JUL-1995
            (J) PUBLICATION DATE: 01-FEB-1996

(xi) SEQUENCE DESCRIPTION:  SEQ ID NO: 93:

GGTTGCTTCC TTCCTCTCTG GTACCC                                              26

(2) INFORMATION FOR SEQ ID NO: 94:

(i) SEQUENCE CHARACTERISTICS:
            (A) LENGTH: 41 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 96/02557 (SEQ ID NO:10)
            (I) FILING DATE: 14-JUL-1995
            (J) PUBLICATION DATE: 01-FEB-1996

(xi) SEQUENCE DESCRIPTION:  SEQ ID NO: 94:

CTAGCAGTGG CGCCCGAACA GGTTCGCCTG TTCGGGCGCC A                              41

(2) INFORMATION FOR SEQ ID NO: 95:

(i) SEQUENCE CHARACTERISTICS:
            (A) LENGTH: 30 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 96/02557 (SEQ ID NO:22)
            (I) FILING DATE: 14-JUL-1995
            (J) PUBLICATION DATE: 01-FEB-1996

(xi) SEQUENCE DESCRIPTION:  SEQ ID NO: 95:

CATCACCTGC CATCTGTTTT CCATAATCCC                                           30

(2) INFORMATION FOR SEQ ID NO: 96:

(i) SEQUENCE CHARACTERISTICS:
            (A) LENGTH: 31 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 96/02557 (SEQ ID NO:23)
            (I) FILING DATE: 14-JUL-1995

(J) PUBLICATION DATE: 01-FEB-1996

(xi) SEQUENCE DESCRIPTION: SEQ ID NO: 96:

CCTGTCTACT TGCCACACAA TCATCACCTG C                                          31

(2) INFORMATION FOR SEQ ID NO: 97:

(i) SEQUENCE CHARACTERISTICS:
        (A) LENGTH: 30 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV (x) PUBLICATION INFORMATION:
        (H) DOCUMENT NUMBER: WO 96/02557 (SEQ ID NO:25)
        (I) FILING DATE: 14-JUL-1995
        (J) PUBLICATION DATE: 01-FEB-1996

(xi) SEQUENCE DESCRIPTION: SEQ ID NO: 97:

ACTATTGCTA TTATTATTGC TACTACTAAT                                             30

(2) INFORMATION FOR SEQ ID NO: 98:

(i) SEQUENCE CHARACTERISTICS:
        (A) LENGTH: 26 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV (x) PUBLICATION INFORMATION:
        (H) DOCUMENT NUMBER: WO 95/03406 (SEQ ID NO:1)
        (I) FILING DATE: 19-JUL-1994
        (J) PUBLICATION DATE: 02-FEB-1995

(xi) SEQUENCE DESCRIPTION: SEQ ID NO: 98:

CTTCGGGCCT GTCGGGTCCC CTCGGG                                                 26

(2) INFORMATION FOR SEQ ID NO: 99:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to HIV (x) PUBLICATION INFORMATION:
        (H) DOCUMENT NUMBER: WO 95/03406 (SEQ ID NO:2)
        (I) FILING DATE: 19-JUL-1994
        (J) PUBLICATION DATE: 02-FEB-1995

(xi) SEQUENCE DESCRIPTION: SEQ ID NO: 99:

CUUCGGGCCU GUCGGGUCCC UCGGG                                                  25

(2) INFORMATION FOR SEQ ID NO: 100:

(i) SEQUENCE CHARACTERISTICS:

(A) LENGTH: 14 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 95/03406 (SEQ ID NO:3)
            (I) FILING DATE: 19-JUL-1994
            (J) PUBLICATION DATE: 02-FEB-1995

(xi) SEQUENCE DESCRIPTION:  SEQ ID NO: 100:

GCCTGTCGGG TCCC                                                            14

(2) INFORMATION FOR SEQ ID NO: 101:

(i) SEQUENCE CHARACTERISTICS:
            (A) LENGTH: 14 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 95/03406 (SEQ ID NO:4)
            (I) FILING DATE: 19-JUL-1994
            (J) PUBLICATION DATE: 02-FEB-1995

(xi) SEQUENCE DESCRIPTION:  SEQ ID NO: 101:

GCCUGUCGGG UCCC                                                            14

(2) INFORMATION FOR SEQ ID NO: 102:

(i) SEQUENCE CHARACTERISTICS:
            (A) LENGTH: 26 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV (x) PUBLICATION INFORMATION:
            (H) DOCUMENT NUMBER: WO 95/03406 (SEQ ID NO:5)
            (I) FILING DATE: 19-JUL-1994
            (J) PUBLICATION DATE: 02-FEB-1995

(xi) SEQUENCE DESCRIPTION:  SEQ ID NO: 102:

CTTCGGGCCT GTCGGGTCCC CTCGGG                                               26

(2) INFORMATION FOR SEQ ID NO: 103:

(i) SEQUENCE CHARACTERISTICS:
            (A) LENGTH: 26 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to HIV -continued

```
     (x) PUBLICATION INFORMATION:
         (H) DOCUMENT NUMBER: WO 95/03406 (SEQ ID NO:6)
         (I) FILING DATE: 19-JUL-1994
         (J) PUBLICATION DATE: 02-FEB-1995

(xi) SEQUENCE DESCRIPTION:  SEQ ID NO: 103:

GCTGGTGATC CTTTCCATCC CTGTGG                                        26

(2) INFORMATION FOR SEQ ID NO: 104:

(i) SEQUENCE CHARACTERISTICS:
         (A) LENGTH: 8 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to HIV; a.k.a.
             "ISIS 5320"

(x) PUBLICATION INFORMATION:
         (H) DOCUMENT NUMBER: US 5523389
         (I) FILING DATE: 28-SEP-1994
         (J) PUBLICATION DATE: 04-JUN-1995

(xi) SEQUENCE DESCRIPTION:  SEQ ID NO: 104:

TTGGGGTT                                                             8

(2) INFORMATION FOR SEQ ID NO: 105:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to Hepatitis C Virus;
             a.k.a. "ISIS 6547"

(x) PUBLICATION INFORMATION:
         (A) AUTHORS: Hanecak, R., et al.
         (B) TITLE: Intramolecular G-quartet Motifs Confer
             Nuclease Resistance to a Potent Anti-HIV
             Oligonucleotide
         (C) JOURNAL: Journal of Virology
         (D) VOLUME: 70
         (E) ISSUE: 8
         (F) PAGES: 5203-5212
         (G) DATE: 01-AUG-1996

(xi) SEQUENCE DESCRIPTION:  SEQ ID NO: 105:

GTGCTCATGG TGCACGGTCT                                               20

(2) INFORMATION FOR SEQ ID NO: 106:

(i) SEQUENCE CHARACTERISTICS:
         (A) LENGTH: 20 base pairs
         (B) TYPE: Nucleic Acid
         (C) STRANDEDNESS: Single
         (D) TOPOLOGY: Linear (iv) ANTI-SENSE: Yes (ix) FEATURE:
         (D) OTHER INFORMATION: Antisense to influenza virus (x) PUBLICATION INFORMATION:
         (H) DOCUMENT NUMBER: WO 91/16902 (SEQ ID NO:1)
```

(I) FILING DATE: 29-APR-1991
        (J) PUBLICATION DATE: 14-NOV-1991

(xi) SEQUENCE DESCRIPTION: SEQ ID NO: 106:

CATTCAAATG GTTTGCCTGC                                                    20

(2) INFORMATION FOR SEQ ID NO: 107:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:2)
        (I) FILING DATE: 29-APR-1991
        (J) PUBLICATION DATE: 14-NOV-1991

(xi) SEQUENCE DESCRIPTION: SEQ ID NO: 107:

GCAGGCAAAC CATTTGAATG                                                    20

(2) INFORMATION FOR SEQ ID NO: 108:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:3)
        (I) FILING DATE: 29-APR-1991
        (J) PUBLICATION DATE: 14-NOV-1991

(xi) SEQUENCE DESCRIPTION: SEQ ID NO: 108:

CCATAATCCC CTGCTTCTGC                                                    20

(2) INFORMATION FOR SEQ ID NO: 109:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:4)
        (I) FILING DATE: 29-APR-1991
        (J) PUBLICATION DATE: 14-NOV-1991

(xi) SEQUENCE DESCRIPTION: SEQ ID NO: 109:

GCAGAAGCAG GGGATTATGG                                                    20

(2) INFORMATION FOR SEQ ID NO: 110:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:5)
        (I) FILING DATE: 29-APR-1991
        (J) PUBLICATION DATE: 14-NOV-1991

(xi) SEQUENCE DESCRIPTION:   SEQ ID NO: 110:

GCAGAAGCAG AGGATTATGG                                                    20

(2) INFORMATION FOR SEQ ID NO: 111:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:6)
        (I) FILING DATE: 29-APR-1991
        (J) PUBLICATION DATE: 14-NOV-1991

(xi) SEQUENCE DESCRIPTION:   SEQ ID NO: 111:

GCATAAGCAG AGGATCATGG                                                    20

(2) INFORMATION FOR SEQ ID NO: 112:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:7)
        (I) FILING DATE: 29-APR-1991
        (J) PUBLICATION DATE: 14-NOV-1991

(xi) SEQUENCE DESCRIPTION:   SEQ ID NO: 112:

GGCAAGCTTT ATTGAGGCTT                                                    20

(2) INFORMATION FOR SEQ ID NO: 113:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus -continued

```
    (x) PUBLICATION INFORMATION:
        (H) DOCUMENT NUMBER: WO 91/16902 (SEQ ID NO:8)
        (I) FILING DATE: 29-APR-1991
        (J) PUBLICATION DATE: 14-NOV-1991

(xi) SEQUENCE DESCRIPTION:  SEQ ID NO: 113:

ATCTTCATCA TCTGAGAGAT                                                   20

(2) INFORMATION FOR SEQ ID NO: 114:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to influenza virus (x) PUBLICATION INFORMATION:
        (H) DOCUMENT NUMBER: WO 91/16902 (SEQ ID NO:9)
        (I) FILING DATE: 29-APR-1991
        (J) PUBLICATION DATE: 14-NOV-1991

(xi) SEQUENCE DESCRIPTION:  SEQ ID NO: 114:

CGTAAGCAAC AGTAGTCCTA                                                   20

(2) INFORMATION FOR SEQ ID NO: 115:

(i) SEQUENCE CHARACTERISTICS:
        (A) LENGTH: 25 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Epstein-Barr Virus (x) PUBLICATION INFORMATION:
        (H) DOCUMENT NUMBER: WO 95/22554 (SEQ ID NO:1)
        (I) FILING DATE: 17-FEB-1995
        (J) PUBLICATION DATE: 24-AUG-1995

(xi) SEQUENCE DESCRIPTION:  SEQ ID NO: 115:

TTTGGGTCCA TCATCTTCAG CAAAG                                             25

(2) INFORMATION FOR SEQ ID NO: 116:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Epstein-Barr Virus (x) PUBLICATION INFORMATION:
        (H) DOCUMENT NUMBER: WO 95/22554 (SEQ ID NO:2)
        (I) FILING DATE: 17-FEB-1995
        (J) PUBLICATION DATE: 24-AUG-1995

(xi) SEQUENCE DESCRIPTION:  SEQ ID NO: 116:

CATCATCTTC AGCAAAGATA                                                   20
```

(2) INFORMATION FOR SEQ ID NO: 117:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Epstein-Barr Virus (x) PUBLICATION INFORMATION:
        (H) DOCUMENT NUMBER: WO 95/22554 (SEQ ID NO:3)
        (I) FILING DATE: 17-FEB-1995
        (J) PUBLICATION DATE: 24-AUG-1995

(xi) SEQUENCE DESCRIPTION: SEQ ID NO: 117:

TCAGAAGTCG AGTTTGGGTC                                          20

(2) INFORMATION FOR SEQ ID NO: 118:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Respiratory
            Syncytial Virus (x) PUBLICATION INFORMATION:
        (H) DOCUMENT NUMBER: WO 95/22553 (SEQ ID NO:1)
        (I) FILING DATE: 17-FEB-1995
        (J) PUBLICATION DATE: 24-AUG-1995

(xi) SEQUENCE DESCRIPTION: SEQ ID NO: 118:

ACGCGAAAAA ATGCGTACAA                                          20

(2) INFORMATION FOR SEQ ID NO: 119:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to Respiratory
            Syncytial Virus (x) PUBLICATION INFORMATION:
        (H) DOCUMENT NUMBER: WO 95/22553 (SEQ ID NO:2)
        (I) FILING DATE: 17-FEB-1995
        (J) PUBLICATION DATE: 24-AUG-1995

(xi) SEQUENCE DESCRIPTION: SEQ ID NO: 119:

TAAACCAAAA AAATGGGGCA                                          20

(2) INFORMATION FOR SEQ ID NO: 120:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear

```
    (iv) ANTI-SENSE: Yes (ix) FEATURE:
         (D) OTHER INFORMATION: Antisense to Respiratory
             Syncytial Virus (x) PUBLICATION INFORMATION:
        (H) DOCUMENT NUMBER: WO 95/22553 (SEQ ID NO:3)
        (I) FILING DATE: 17-FEB-1995
        (J) PUBLICATION DATE: 24-AUG-1995

(xi) SEQUENCE DESCRIPTION: SEQ ID NO: 120:

AAATGGGGCA AATAAGAATT                                            20

(2) INFORMATION FOR SEQ ID NO: 121:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
         (D) OTHER INFORMATION: Antisense to Respiratory
             Syncytial Virus (x) PUBLICATION INFORMATION:
        (H) DOCUMENT NUMBER: WO 95/22553 (SEQ ID NO:4)
        (I) FILING DATE: 17-FEB-1995
        (J) PUBLICATION DATE: 24-AUG-1995

(xi) SEQUENCE DESCRIPTION: SEQ ID NO: 121:

AAAAATGGGG CAAATAAATC                                            20

(2) INFORMATION FOR SEQ ID NO: 122:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
         (D) OTHER INFORMATION: Antisense to cytomagalovirus intron-
             exon boundary of genes UL36 and UL37; a.k.a. "UL36ANTI"
             and "GEM 132"

(x) PUBLICATION INFORMATION:
        (A) AUTHORS: Pari, G.S., et al.
        (B) TITLE: Potent Antiviral Activity of an Antisense
             Oligonucleotide Complementary to the Intron-Exon
             Boundary of Human Cytomegalovirus Genes UL36 and UL37
        (C) JOURNAL: Antimicrobial Agents and Chemotherapy
        (D) VOLUME: 39
        (E) ISSUE: 5
        (F) PAGES: 1157-1161
        (G) DATE: MAY-1995

(x) PUBLICATION INFORMATION:
        (H) DOCUMENT NUMBER: WO 95/32213 (SEQ ID NO:1)
        (I) FILING DATE: 19-MAY-1995
        (J) PUBLICATION DATE: 30-NOV-1995

(xi) SEQUENCE DESCRIPTION: SEQ ID NO: 122:

TGGGGCTTAC CTTGCGAACA                                            20

(2) INFORMATION FOR SEQ ID NO: 123:
```

-continued

```
   (i) SEQUENCE CHARACTERISTICS:
       (A) LENGTH: 20 base pairs
       (B) TYPE: Nucleic Acid
       (C) STRANDEDNESS: Single
       (D) TOPOLOGY: Linear (iv) ANTI-SENSE: Yes (ix) FEATURE:
       (D) OTHER INFORMATION: Antisense to cytomagalovirus (x) PUBLICATION INFORMATION:
       (H) DOCUMENT NUMBER: WO 95/32213 (SEQ ID NO:2)
       (I) FILING DATE: 19-MAY-1995
       (J) PUBLICATION DATE: 30-NOV-1995

(xi) SEQUENCE DESCRIPTION:   SEQ ID NO: 123:

GACGTGGGGC TTACCTTGCG                                                20

(2) INFORMATION FOR SEQ ID NO: 124:

(i) SEQUENCE CHARACTERISTICS:
       (A) LENGTH: 20 base pairs
       (B) TYPE: Nucleic Acid
       (C) STRANDEDNESS: Single
       (D) TOPOLOGY: Linear (iv) ANTI-SENSE: Yes (ix) FEATURE:
       (D) OTHER INFORMATION: Antisense to cytomagalovirus (x) PUBLICATION INFORMATION:
       (H) DOCUMENT NUMBER: WO 95/32213 (SEQ ID NO:3)
       (I) FILING DATE: 19-MAY-1995
       (J) PUBLICATION DATE: 30-NOV-1995

(xi) SEQUENCE DESCRIPTION:   SEQ ID NO: 124:

TCTTCAACGA CGTGGGGCTT                                                20

(2) INFORMATION FOR SEQ ID NO: 125:

(i) SEQUENCE CHARACTERISTICS:
       (A) LENGTH: 21 base pairs
       (B) TYPE: Nucleic Acid
       (C) STRANDEDNESS: Single
       (D) TOPOLOGY: Linear (iv) ANTI-SENSE: Yes (ix) FEATURE:
       (D) OTHER INFORMATION: Antisense to cytomagalovirus (x) PUBLICATION INFORMATION:
       (H) DOCUMENT NUMBER: WO 95/32213 (SEQ ID NO:4)
       (I) FILING DATE: 19-MAY-1995
       (J) PUBLICATION DATE: 30-NOV-1995

(xi) SEQUENCE DESCRIPTION:   SEQ ID NO: 125:

GACGCGTGGC ATGCTTGGTG T                                              21

(2) INFORMATION FOR SEQ ID NO: 126:

(i) SEQUENCE CHARACTERISTICS:
       (A) LENGTH: 21 base pairs
       (B) TYPE: Nucleic Acid
       (C) STRANDEDNESS: Single
       (D) TOPOLOGY: Linear (iv) ANTI-SENSE: Yes (ix) FEATURE:
       (D) OTHER INFORMATION: Antisense to cytomagalovirus
```

```
        (x) PUBLICATION INFORMATION:
            (H) DOCUMENT NUMBER: WO 95/32213 (SEQ ID NO:5)
            (I) FILING DATE: 19-MAY-1995
            (J) PUBLICATION DATE: 30-NOV-1995

(xi) SEQUENCE DESCRIPTION: SEQ ID NO: 126:

AGGTTGGGGT CGACGCGTGG C                                              21

(2) INFORMATION FOR SEQ ID NO: 127:

(i) SEQUENCE CHARACTERISTICS:
            (A) LENGTH: 21 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to cytomagalovirus (x) PUBLICATION INFORMATION:
            (H) DOCUMENT NUMBER: WO 95/32213 (SEQ ID NO:6)
            (I) FILING DATE: 19-MAY-1995
            (J) PUBLICATION DATE: 30-NOV-1995

(xi) SEQUENCE DESCRIPTION: SEQ ID NO: 127:

GGCTGAGCGG TCATCCTCGG A                                              21

(2) INFORMATION FOR SEQ ID NO: 128:

(i) SEQUENCE CHARACTERISTICS:
            (A) LENGTH: 20 base pairs
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to cytomagalovirus (x) PUBLICATION INFORMATION:
            (H) DOCUMENT NUMBER: WO 95/32213 (SEQ ID NO:7)
            (I) FILING DATE: 19-MAY-1995
            (J) PUBLICATION DATE: 30-NOV-1995

(xi) SEQUENCE DESCRIPTION: SEQ ID NO: 128:

CGGGACTCAC CGTCGTTCTG                                                20

(2) INFORMATION FOR SEQ ID NO: 129:

(i) SEQUENCE CHARACTERISTICS:
            (A) LENGTH: 20
            (B) TYPE: Nucleic Acid
            (C) STRANDEDNESS: Single
            (D) TOPOLOGY: Linear (iv) ANTI-SENSE: Yes (ix) FEATURE:
            (D) OTHER INFORMATION: Antisense to cytomagalovirus (x) PUBLICATION INFORMATION:
            (H) DOCUMENT NUMBER: WO 95/32213 (SEQ ID NO:8)
            (I) FILING DATE: 19-MAY-1995
            (J) PUBLICATION DATE: 30-NOV-1995

(xi) SEQUENCE DESCRIPTION: SEQ ID NO: 129:

GGAGGAGAGC CTACAGACGG                                                20
```

(2) INFORMATION FOR SEQ ID NO: 130:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to cytomagalovirus (x) PUBLICATION INFORMATION:
        (H) DOCUMENT NUMBER: WO 95/32213 (SEQ ID NO:9)
        (I) FILING DATE: 19-MAY-1995
        (J) PUBLICATION DATE: 30-NOV-1995

(xi) SEQUENCE DESCRIPTION: SEQ ID NO: 130:

AGTAACGCAC CGTCGGTGCC                                          20

(2) INFORMATION FOR SEQ ID NO: 131:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to cytomegalovirus;
            a.k.a. "ISIS 2922"

(x) PUBLICATION INFORMATION:
        (H) DOCUMENT NUMBER: US 5442049 (SEQ ID NO:22)
        (I) FILING DATE: 25-JAN-1993
        (J) PUBLICATION DATE: 15-AUG-1995

(xi) SEQUENCE DESCRIPTION: SEQ ID NO: 131:

GCGTTTGCTC TTCTTCTTGC G                                        21

(2) INFORMATION FOR SEQ ID NO: 132:

(i) SEQUENCE CHARACTERISTICS:
        (A) LENGTH: 19 base pairs
        (B) TYPE: Nucleic Acid
        (C) STRANDEDNESS: Single
        (D) TOPOLOGY: Linear (iv) ANTI-SENSE: Yes (ix) FEATURE:
        (D) OTHER INFORMATION: Antisense to VEGF/VPF; a.k.a. "H3"

(x) PUBLICATION INFORMATION:
        (A) AUTHORS: Smyth, A.P., et al.
        (B) TITLE: Antisense Oligonucleotides Inhibit Vascular
            Endothelial Growth Factor/vascular Permeability Factor
            Expression in Normal Human Epidermal Keratinocytes
            Boundary of Human Cytomegalovirus Genes UL36 and UL37
        (C) JOURNAL: The Journal of Investigative Dermatology
        (D) VOLUME: 108
        (E) ISSUE: 4
        (F) PAGES: 523-526
        (G) DATE: N/A-APR-1997

(xi) SEQUENCE DESCRIPTION: SEQ ID NO: 132:

CACCCAAGAC AGCAGAAAG                                            19

COMPOSITIONS AND METHODS FOR THE DELIVERY OF OLIGONUCLEOTIDES VIA THE ALIMENTARY CANAL

CROSS-REFERENCE TO RELATED APPLICATIONS

This application is a Continuation-In-Part of U.S. patent application Ser. No. 08/886,829, filed Jul. 1, 1997.

FIELD OF THE INVENTION

The present invention relates to compositions and methods which enhance the transport of nucleic acids at various sites in the alimentary canal. More particularly, the methods and compositions enhance the transport of oligonucleotides and other nucleic acids across the mucosa of the alimentary canal through the use of one or more penetration enhancers. More specifically, the present invention is directed to the use of various fatty acids, bile salts, chelating agents and other penetration enhancers, as well as carrier compounds, to enhance the stability of oligonucleotides and other nucleic acids and/or their transport across and/or into cells of the alimentary canal. More specific objectives and advantages of the invention will hereinafter be made clear or become apparent to those skilled in the art during the course of explanation of preferred embodiments of the invention.

BACKGROUND OF THE INVENTION

Advances in the field of biotechnology have given rise to significant advances in the treatment of previously-intractable diseases such as cancer, genetic diseases, arthritis and AIDS. Many such advances involve the administration of oligonucleotides and other nucleic acids to a subject, particularly a human subject. The administration of such molecules via parenteral routes has been shown to be effective for the treatment of diseases and/or disorders. See, e.g., U.S. Pat. No. 5,595,978, Jan. 21, 1997 to Draper et al., which discloses intravitreal injection as a means for the direct delivery of antisense oligonucleotides to the vitreous humor of the mammalian eye. See also, Robertson, *Nature Biotechnology*, 1997, 15:209 and Anon., *Genetic Engineering News*, 1997, 15:1, each of which discuss the treatment of Crohn's disease via intravenous infusions of antisense oligonucleotides. Oligonucleotides and other nucleic acids have been administered via non-traumatic (non-parenteral) routes such as oral or rectal delivery or other mucosal routes only with difficulty. Facile non-parenteral administration of oligonucleotides and other nucleic acids offers the promise of simpler, easier and less injurious administration of such nucleic acids without the need for sterile procedures and their concomitant expenses, e.g., hospitalization and/or physician fees. There thus remains a need to provide compositions and methods to enhance the alimentary availability of novel drugs such as oligonucleotides. It is desirable that such new compositions and methods provide for the simple, convenient, practical and optimal alimentary delivery of oligonucleotides and other nucleic acids.

OBJECTS OF THE INVENTION

To date, there are no known pharmaceutical compositions which are capable of generally enhancing the oral delivery of oligonucleotides and nucleic acids, particularly oligonucleotides having a variety of chemical modifications. Thus, there is a long-felt need for compositions which can effectively provide for the oral delivery of nucleic acids, particularly oligonucleotides, more particularly oligonucleotides having one or more chemical modifications, together with methods for using such compositions to deliver such oligonucleotides and nucleic acids into an animal via the alimentary canal, e.g., via oral or rectal administration. It is desirable that such new compositions and methods provide for the simple, convenient, practical and optimal introduction of transport and delivery of oligonucleotides and other nucleic acids across epithelial cells at various mucosal sites.

SUMMARY OF THE INVENTION

In accordance with the present invention, compositions and methods are provided for the alimentary delivery and mucosal penetration of nucleic acids in an animal. In particular, the present invention provides compositions and methods for modulating the production of selected proteins or other biological phenomena in an animal, which involves the administration of an oligonucleotide, especially an antisense oligonucleotide, to the alimentary canal of an animal, thereby bypassing the complications and expense which may be associated with intravenous and other modes of in vivo administration. "Administration to the alimentary canal" refers to the contacting, directly or otherwise, to all or a portion of the alimentary canal of an animal.

Because of the advantages of alimentary delivery of drugs of the antisense class, the compositions and methods of the invention can be used in therapeutic methods as explained in more detail herein. However, the compositions and methods herein provided may also be used to examine the function of various proteins and genes in an animal, including those essential to animal development.

DETAILED DESCRIPTION OF PREFERRED EMBODIMENTS

The invention provides compositions and methods for the delivery of oligonucleotides and other nucleic acids to the alimentary canal of an animal. In particular, the present invention provides compositions and methods for modulating the in vivo expression of a gene in an animal through the alimentary canal administration of an antisense oligonucleotide, thereby bypassing the complications and expense which may be associated with intravenous and other routes of administration. Enhanced bioavailability of oligonucleotides and other nucleic acids administered to the alimentary canal of an animal is achieved through the use of the compositions and methods of the invention. The term "bioavailability" refers to a measurement of what portion of an administered drug reaches the circulatory system when a non-parenteral mode of administration is used to introduce the drug into an animal. The term is used for drugs whose efficacy is related to the blood concentration achieved, even if the drug's ultimate site of action is intracellular (van Berge-Henegouwen et al., *Gastroenterol.*, 1977, 73:300). Traditionally, bioavailability studies determine the degree of intestinal absorption of a drug by measuring the change in peripheral blood levels of the drug after an oral dose (DiSanto, Chapter 76 In: *Remington's Pharmaceutical Sciences*, 18th Ed., Gennaro, ed., Mack Publishing Co., Easton, Pa., 1990, pages 1451–1458). The area under the curve ($AUC_o$) is divided by the area under the curve after an intravenous (i.v.) dose ($AUC_{iv}$) and the quotient is used to calculate the fraction of drug absorbed. This approach cannot be used, however, with compounds which have a large "first pass clearance," i.e., compounds for which hepatic uptake is so rapid that only a fraction of the absorbed material enters the peripheral blood. For such compounds, other methods must be used to determine the absolute bioavailability (van Berge-Henegouwen et al., Gastroenterol., 1977, 73:300).

Studies suggest that oligonucleotides are rapidly eliminated from plasma and accumulate mainly in the liver and kidney after i.v. administration (Miyao et al., *Antisense Res. Dev.*, 1995, 5:115; Takakura et al., *Antisense & Nucl. Acid Drug Dev.*, 1996, 6:177). Accordingly, means for measuring and avoiding first pass clearance effects may be needed for the development of effective orally administered pharmaceutical compositions comprising these or other nucleic acids.

Another "first pass effect" that applies to orally administered drugs is degradation due to the action of gastric acid and various digestive enzymes. Furthermore, the entry of many high molecular weight active agents (such as peptides, proteins and oligonucleotides) and some conventional and/or low molecular weight drugs (e.g., insulin, vasopressin, leucine enkephalin, etc.) through mucosal routes (such as oral, nasal, pulmonary, buccal, rectal, transdermal, vaginal and ocular) to the bloodstream is frequently obstructed by poor transport across epithelial cells and concurrent metabolism during transport.

One means of ameliorating first pass clearance effects is to increase the dose of administered drug, thereby compensating for proportion of drug lost to first pass clearance. Although this may be readily achieved with i.v. administration by, for example, simply providing more of the drug to an animal, other factors influence the bioavailability of drugs administered via the alimentary canal. For example, a drug may be enzymatically or chemically degraded in the alimentary canal and/or may be impermeable or semipermeable to alimentary mucosa. It has now been found that oligonucleotides can be introduced effectively into animals via the alimentary canal through coadministration of "mucosal penetration enhancers," also known as "absorption enhancers" or simply as "penetration enhancers". These are substances which facilitate the transport of a drug across the mucous membrane(s) of the alimentary canal associated with the desired mode of administration.

Many pharmaceutically acceptable penetration enhancers are known for use with certain drugs. A "pharmaceutically acceptable" component of a formulation is one which, together with such excipients, diluents, stabilizers, preservatives and other ingredients as are appropriate to the nature, composition and mode of administration of the formulation. Accordingly it is desired to select penetration enhancers which will provide the oligonucleotides to the alimentary canal of a patient in an effective physical form, without interfering with the activity of the oligonucleotides and in an manner such that the same can be introduced into the body of an animal without unacceptable side-effects such as toxicity, irritation or allergic response. As is known in the medical arts, a compound that is not pharmaceutically acceptable for a given patient having a particular disease or disorder may in fact be pharmaceutically acceptable to another patient with a different set of attendant circumstances. For example, a high degree of toxicity might not be acceptable for a patient suffering from a mild, non-life-threatening disorder but be nonetheless pharmaceutically acceptable for a terminally ill patient. As another example, due to differences in human physiology during development, a composition that is pharmaceutically acceptable for most adults might be inappropriate for a child or pregnant woman.

The present invention provides compositions comprising one or more pharmaceutically acceptable alimentary penetration enhancers, and methods of using such compositions, which result in the improved bioavailability of nucleic acids administered via alimentary modes of administration. Heretofore, certain penetration enhancers have been used to improve the bioavailability of certain drugs. See Muranishi, *Crit. Rev. Ther. Drug Carrier Systems*, 1990, 7:1 and Lee et al., *Crit. Rev. Ther. Drug Carrier Systems*, 1991, 8:91. However, it is generally viewed to be the case that effectiveness of such penetration enhancers is unpredictable. Accordingly, it has been surprisingly found that the administration of oligonucleotides, relatively complex molecules which are known to be difficult to administer to animals and man, can be greatly improved in the alimentary canal through the use of a number of different classes of penetration enhancers.

The following portion of this specification provides, in more detail, information concerning (1) modes of administration, (2) penetration enhancers and carriers, (3) oligonucleotides, (4) administration of pharmaceutical compositions, (5) bioequivalents and (6) exemplary utilities of the invention.

1. Modes of Administration: The present invention provides compositions and methods for alimentary delivery of one or more nucleic acids to an animal. For purposes of the invention, the term "animal" is meant to encompass humans as well as other mammals, as well as reptiles, fish, amphibians, and birds. The term "alimentary delivery" refers to the administration, directly or otherwise, to a portion of the alimentary canal of an animal. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastro-intestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

In addition, iontophoresis (transfer of ionic solutes through biological membranes under the influence of an electric field) (Lee et al., *Critical Reviews in Therapeutic Drug Carrier Systems*, 1991, p. 163), phonophoresis or sonophoresis (use of ultrasound to enhance the absorption of various therapeutic agents across biological membranes, notably the skin and the cornea) (Lee et al., Critical Reviews in Therapeutic Drug Carrier Systems, 1991, at p. 166), and optimization of vehicle characteristics relative to dose deposition and retention at the site of administration (Lee et al., *Critical Reviews in Therapeutic Drug Carrier Systems*, 1991, p. 168) may be useful to enhance the transport of drugs across mucosal sites.

A. Buccal/Sublingual Administration: Delivery of a drug via the oral mucosa has several desirable features, including, in many instances, a more rapid rise in plasma concentration of the drug than via oral delivery (Harvey, Chapter 35 In: *Remington's Pharmaceutical Sciences*, 18th Ed., Gennaro, ed., Mack Publishing Co., Easton, Pa., 1990, page 711). Furthermore, because venous drainage from the mouth is to the superior vena cava, this route also bypasses rapid first-pass metabolism by the liver. Both of these features contribute to the sublingual route being the mode of choice for nitroglycerin (Benet et al., Chapter 1 In: *Goodman & Gilman's* The Pharmacological Basis of Therapeutics, 9th Ed., Hardman et al., eds., McGraw-Hill, New York, N.Y., 1996, page 7).

B. Endoscopic Administration: Endoscopy can be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., Gan To Kagaku Ryoho, 1992, 19(10 Suppl.):1591). Pharmaceutical compositions, including liposomal formulations, can be delivered directly into portions of the alimentary canal, such as, e.g., the duodenum (Somogyi et al., *Pharm. Res.*, 1995, 12, 149) or the gastric submucosa (Akamo et al., *Japanese J. Cancer Res.*, 1994, 85, 652) via endoscopic means. Gastric lavage devices (Inoue et al., *Artif. Organs*, 1997, 21, 28) and percutaneous endoscopic feeding devices (Pennington et al., *Ailment Pharmacol. Ther.*, 1995, 9, 471) can also be used for direct alimentary delivery of pharmaceutical compositions.

C. Rectal Administration: Drugs administered by the oral route can often be alternatively administered by the lower enteral route, i.e., through the anal portal into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration may result in more prompt and higher blood levels than the oral route, but the converse may be true as well (Harvey, Chapter 35 In: *Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: Goodman & Gilman's *The Pharmacological Basis of Therapeutics*, 9th Ed., Hardman et al., eds., McGraw-Hill, New York, N.Y., 1996).

D. Oral Administration: The preferred method of administration is oral delivery, which is typically the most convenient route for access to the systemic circulation. Absorption from the alimentary canal is governed by factors that are generally applicable, e.g., surface area for absorption, blood flow to the site of absorption, the physical state of the drug and its concentration at the site of absorption (Benet et al., Chapter 1 In: Goodman & Gilman's *The Pharmacological Basis of Therapeutics*, 9th Ed., Hardman et al., eds., McGraw-Hill, New York, N.Y., 1996, pages 5–7). A significant factor which may limit the oral bioavailability of a drug is the degree of "first pass effects." For example, some substances have such a rapid hepatic uptake that only a fraction of the material absorbed enters the peripheral blood (Van Berge-Henegouwen et al., *Gastroenterology*, 1977, 73:300). The compositions and methods of the invention circumvent, at least partially, such first pass effects by providing improved uptake of nucleic acids and thereby, e.g., causing the hepatic uptake system to become saturated and allowing a significant portion of the nucleic acid so administered to reach the peripheral circulation. Additionally or alternatively, the hepatic uptake system is saturated with one or more inactive "carrier" nucleic acids prior to administration of the active nucleic acid.

2. Penetration Enhancers and Carriers: The present invention employs various penetration enhancers in order to effect the gastrointestinal delivery of nucleic acids, particularly oligonucleotides. Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p. 92). Each of these classes is discussed in more detail in the following sections. Carrier substances (or simply "carriers"), which reduce first pass effects by, e.g., saturating the hepatic uptake system, are also herein described.

A. Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the alimentary mucosa is enhanced. In addition to bile salts and fatty acids, these penetration enhancers include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorohemical emulsions, such as FC-43 (Takahashi et al., *J. Pharm. Phamacol.*, 1988, 40:252).

B. Fatty Acids: Various fatty acids and their derivatives which act as penetration enhancers include, for example, oleic acid, lauric acid, capric acid (a.k.a. n-decanoic acid), myristic acid, palmitic acid, stearic acid, linoleic acid, linolenic acid, dicaprate, tricaprate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7:1; El-Hariri et al., *J. Pharm. Pharmacol.*, 1992, 44:651).

C. Bile Salts: The physiological roles of bile include the facilitation of dispersion and absorption of lipids and fat-soluble vitamins (Brunton, Chapter 38 In: Goodman & Gilman's *The Pharmacological Basis of Therapeutics*, 9th Ed., Hardman et al., eds., McGraw-Hill, New York, N.Y., 1996, pages 934–935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7:1; Yamamoto et al., *J. Pharm. Exp. Ther.*, 1992, 263:25; Yamashita et al., *J. Pharm. Sci.*, 1990, 79:579).

D. Chelating Agents: Chelating agents, as used in connection with the present invention, can be defined to be compounds that remove metallic ions from solution by forming complexes therewith, with the result that absorption of oligonucelotides through the alimentary mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7:1; Buur et al., *J. Control Rel.*, 1990, 14:43).

E. Non-Chelating Non-Surfactants: As used herein, non-chelating non-surfactant penetration enhancing compounds can be defined as compounds that demonstrate insignificant activity as chelating agents or as surfactants but that nonetheless enhance absorption of oligonucelotides through the alimentary mucosa (Muranishi, *Critical Reviews in Therapeutic Drug Carrier Systems*, 1990, 7:1). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39:621).

F. Carrier Compounds: As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5:115; Takakura et al., *Antisense & Nucl. Acid Drug Dev.*, 1996, 6:177).

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions of the present invention may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

3. Oligonucleotides: The present invention employs oligonucleotides for use in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, turnover or degradation of the mRNA and possibly even independent catalytic activity which may be engaged in by the RNA. The overall effect of such interference with mRNA function is modulation of the expression of a protein, wherein "modulation" means either an increase (stimulation) or a decrease (inhibition) in the expression of the protein. In the context of the present invention, inhibition is the preferred form of modulation of gene expression.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of repeating units generically known as a nucleotides. An unmodified (naturally occurring) nucleotide has three components: (1) a nitrogenous base linked by one of its nitrogen atoms to (2) a 5-carbon cyclic sugar and (3) a phosphate, esterified to carbon 5 of the sugar. When incorporated into an oligonucleotide chain, the phosphate of a first nucleotide is also esterified to carbon 3 of the sugar of a second, adjacent nucleotide. The "backbone" of an unmodified oligonucleotide consists of (2) and (3), that is, sugars linked together by phosphodiester linkages between the carbon 5 (5') position of the sugar of a first nucleotide and the carbon 3 (3') position of a second, adjacent nucleotide. A "nucleoside" is the combination of (1) a nucleobase and (2) a sugar in the absence of (3) a phosphate moiety (Kornberg, A., *DNA Replication*, W.H. Freeman & Co., San Francisco, 1980, pages 4–7). The backbone of an oligonucleotide positions a series of bases in a specific order; the written representation of this series of bases, which is conventionally written in 5' to 3' order, is known as a nucleotide sequence.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." In the context of the invention, "hybridization" means hydrogen bonding, which may be Watson-Crick, Hoogsteen or reversed Hoogsteen hydrogen bonding, between complementary nucleotides. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that an oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA to cause a decrease or loss of function, and there is a sufficient degree of complementarity to avoid non-specific binding of the oligonucleotide to non-target sequences under conditions in which specific binding is desired, i.e., under physiological conditions in the case of in vivo assays or therapeutic treatment, or in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses. For example, the following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098,890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenzavirus. U.S. Pat. No. 4,806,463 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections. Other examples of antisense oligonucleotides are provided herein.

The oligonucleotides in accordance with this invention preferably comprise from about 8 to about 30 nucleotides. It is more preferred that such oligonucleotides comprise from about 15 to 25 nucleotides. As is known in the art, a nucleotide is a base-sugar combination suitably bound to an adjacent nucleotide through a phosphodiester, phosphorothioate or other covalent linkage. In the context of this invention, the term "oligonucleotide" includes oligonucleotides composed of naturally-occurring nucleobases, sugars and covalent intersugar (backbone) linkages as well as oligonucleotides having non-naturally-occurring portions which function similarly. Such modified or substituted oligonucleotides may be preferred over native forms because of desirable properties such as, for example, enhanced cellular uptake, enhanced binding to target and increased stability in the presence of nucleases.

Oligonucleotides are also useful in determining the nature, function and potential relationship to body or disease states in animals of various genetic components of the body. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences*, 1994, 15:250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. By providing compositions and methods for the simple alimentary delivery of oligonucleotides and other nucleic acids, the present invention overcomes these and other shortcomings.

A. Modified Linkages: Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ (known as a methylene(methylimino) or MMI backbone), $CH_2$—O—N($CH_3$)—$CH_2CH$—N($CH$)$_3$N($CH$)$_3CH_2$ and O—N($CH_3$)—$CH_2$—$CH_2$ backbones, wherein the native phosphodiester backbone is represented as O—P—O—$CH_2$. Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*) —NR—CH$_2$—CH$_2$ and CH$_2$—C(*)—NR—CH$_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science,* 1991, 254:1497; U.S. Pat. No. 5,539,082).

B. Modified Nucleobases: The oligonucleotides of the invention may additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 2-aminoadenine, 2-thiouracil, 2-thiothymine, 5-bromouracil, 5-hydroxymethyluracil, 8-azaguanine, 7-deazaguanine, N$^6$(6-aminohexyl)adenine and 2,6-diaminopurine (Kornberg, A., *DNA Replication, W.H. Freeman & Co., San Francisco,* 1980, pages 75–77; Gebeyehu, G., et al., *Nucleic Acids Res.*, 1987, 15, 4513).

C. Sugar Modifications: The oligonucleotides of the invention may additionally or alternatively comprise substitutions of the sugar portion of the individual nucleotides. For example, oligonucleotides may also have sugar mimetics such as cyclobutyls in place of the pentofuranosyl group. Other preferred modified oligonucleotides may contain one or more substituted sugar moieties comprising one of the following at the 2' position: OH, SH, SCH$_3$, F, OCN, OCH$_3$OCH$_3$, OCH$_3$O(CH$_2$)$_n$CH$_3$, O(CH$_2$)$_2$NH$_2$ or O(CH$_2$)$_n$CH$_3$ where n is from 1 to about 10; C$_1$ to C$_{10}$ lower alkyl, alkoxyalkoxy, substituted lower alkyl, alkaryl or aralkyl; Cl; Br; CN; CF$_3$; OCF$_3$; O-, S-, or N- alkyl; O-, S-, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy (2'-O-CH$_2$CH$_2$OCH$_3$, also known as 2'-O-(2-methoxyethyl)) (Martin et al., *Helv. Chim. Acta,* 1995, 78:486). Other preferred modifications include 2'-methoxy-(2'-O-CH$_3$), 2'-propoxy-(2'-OCH$_2$CH$_2$CH$_3$) and 2'-fluoro-(2'-F).

D. Other Modifications: Similar modifications may also be made at other positions on the oligonucleotide, particularly the 3' position of the sugar on the 3' terminal nucleotide and the 5' position of the 5' terminal nucleotide. The 5' and 3' termini of an oligonucleotide may also be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued May 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers may be used to conjugate an effector group to an oligonucleotide of the invention. As an example, U.S. Pat. No. 5,578,718 to Cook et al. discloses methods of attaching an alkylthio linker, which may be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (Methods in Molecular Biology, Volume 26) Agrawal, S., ed., Humana Press, Totowa, N.J., 1994.

Another preferred additional or alternative modification of the oligonucleotides of the invention involves chemically linking to the oligonucleotide one or more lipophilic moieties which enhance the cellular uptake of the oligonucleotide. Such lipophilic moieties may be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The N$^6$ position of a purine nucleobase may also be utilized to link a lipophilic moiety to an oligonucleotide of the invention (Gebeyehu, G., et al., *Nucleic Acids Res.,* 1987, 15:4513). Such lipophilic moieties include but are not limited to a cholesteryl moiety (Letsinger et al., *Proc. Natl. Acad. Sci. U.S.A.,* 1989, 86:6553), cholic acid (Manoharan et al., *Bioorg. Med. Chem. Let.,* 1994, 4:1053), a thioether, e.g., hexyl-S-tritylthiol (Manoharan et al., *Ann. N.Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., EMO J., 1991, 10:111; Kabanov et al., FEBS Lett., 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Oligonucleotides comprising lipophilic moieties, and methods for preparing such oligonucleotides, are disclosed in U.S. Pat. Nos. 5,138,045, 5,218,105 and 5,459,255, the contents of which are hereby incorporated by reference.

The present invention also includes oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoamidate or phosphotriester linkages (Cook, U.S. Pat. Nos. 5,212,295 and 5,521,302).

E. Chimeric Oligonucleotides: The present invention also includes oligonucleotides which are chimeric. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" may be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy-substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy-substituted), or vice-versa.

F. Incorporation by Reference: The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives. Teachings regarding the synthesis of particular modified oligonucleotides are hereby incorporated by reference from the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having P-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,68,046, drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to methods of synthesizing 2'-fluoro-oligonucleotides.

4. Administration of Pharmaceutical Compositions: The formulation of pharmaceutical compositions and their subsequent administration is believed to be within the skill of those in the art. Specific comments regarding the present invention are presented below.

A. Therapeutic Considerations: In general, for therapeutic applications, a patient (i.e., an animal, including a human, having or predisposed to a disease or disorder) is administered one or more nucleic acids, including oligonucleotides, in accordance with the invention in a pharmaceutically acceptable carrier in doses ranging from 0.01 ug to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the nucleic acid may either be increased in the event the patient does not respond significantly to current dosage levels, or the dose may be decreased if an alleviation of the symptoms of the disorder or disease state is observed, or if the disorder or disease state has been ablated.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 $\mu$g to 100 g per kg of body weight, and may be given once or more daily, weekly, monthly or yearly, or even once every 2 to 20 years. An optimal dosing schedule is used to deliver a therapeutically effective amount of the nucleic acid being administered via a particular mode of administration.

The term "therapeutically effective amount," for the purposes of the invention, refers to the amount of nucleic acid-containing formulation which is effective to achieve an intended purpose without undesirable side effects (such as toxicity, irritation or allergic response). Although individual needs may vary, determination of optimal ranges for effective amounts of formulations is within the skill of the art. Human doses can be extrapolated from animal studies (Katocs et al., Chapter 27 In: *Remington's Pharmaceutical Sciences*, 18th Ed., Gennaro, ed., Mack Publishing Co., Easton, Pa., 1990). Generally, the dosage required to provide an effective amount of a formulation, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: *Goodman & Gilman's The Pharmacological Basis of Therapeutics*, 9th Ed., Hardman et al., eds., McGraw-Hill, New York, N.Y., 1996).

As used herein, the term "high risk individual" is meant to refer to an individual for whom it has been determined, via, e.g., individual or family history or genetic testing, has a significantly higher than normal probability of being susceptible to the onset or recurrence of a disease or disorder. As art of treatment regimen for a high risk individual, the individual can be prophylactically treated to prevent the onset or recurrence of the disease or disorder. The term "prophylactically effective amount" is meant to refer to an amount of a formulation which produces an effect observed as the prevention of the onset or recurrence of a disease or disorder. Prophylactically effective amounts of a formulation are typically determined by the effect they have compared to the effect observed when a second formulation lacking the active agent is administered to a similarly situated individual.

Following successful treatment, it may be desirable to have the patient undergo maintenance therapy to prevent the recurrence of the disease state, wherein the nucleic acid is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

B. Formulation Additives: Formulations for non-parenteral administration of nucleic acids may include sterile aqueous solutions which may also contain buffers, diluents and other suitable additives. Pharmaceutically acceptable organic or inorganic carrier substances suitable for non-parenteral administration which do not deleteriously react with nucleic acids can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The formulations can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with the nucleic acid(s) of the formulation. Aqueous suspensions may contain substances which increase the viscosity of the suspension including, for example, sodium carboxymethylcellulose, sorbitol and/or dextran. Optionally, the suspension may also contain stabilizers.

In one embodiment of the invention, a nucleic acid is administered via the rectal mode. In particular, compositions for rectal administration include foams, solutions (enemas) and suppositories. Rectal suppositories for adults are usually tapered at one or both ends and typically weigh about 2 g each, with infant rectal suppositories typically weighing about one-half as much, when the usual base, cocoa butter, is used (Block, Chapter 87 In: *Remington's Pharmaceutical Sciences,* 18th Ed., Gennaro, ed., Mack Publishing Co., Easton, Pa., 1990).

In a preferred embodiment of the invention, one or more nucleic acids are administered via oral delivery. Compositions for oral administration include powders or granules, suspensions or solutions in water or non-aqueous media, capsules, sachets, troches, tablets or SECs (soft elastic capsules or "caplets"). Thickeners, flavoring agents, diluents, emulsifiers, dispersing aids, carrier substances or binders may be desirably added to such formulations. The use of such formulations has the effect of delivering the nucleic acid to the alimentary canal for exposure to the mucosa thereof. Accordingly, the formulation can consist of material effective in protecting the nucleic acid from pH extremes of the stomach, or in releasing the nucleic acid over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing formulations for alimentary delivery are well known in the art. See, generally, Nairn, Chapter 83; Block, Chapter 87; Rudnic et al., Chapter 89; Porter, Chapter 90; and Longer et al., Chapter 91 In: *Remington's Pharmaceutical Sciences,* 18th Ed., Gennaro, ed., Mack Publishing Co., Easton, Pa., 1990. The formulations of the invention can be converted in a known manner into the customary formulations, such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5% to about 95% by weight of the total mixture, that is to say in amounts which are sufficient to achieve the stated dosage range. The formulations are prepared, for example, by extending the active compounds with solvents and/or excipients, if appropriate using emulsifying agents and/or dispersing agents, and, for example, in the case where water is used as the diluent, organic solvents can be used as auxiliary solvents if appropriate. Compositions may be formulated in a conventional manner using additional pharmaceutically acceptable carriers or excipients as appropriate. Thus, the composition may be prepared by conventional means with additional carriers or excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets may be coated by methods well known in the art. The preparations may also contain flavoring, coloring and/or sweetening agents as appropriate.

The pharmaceutical formulations, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

Formulations of the present invention suitable for oral administration may be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet may be made by compression or molding, optionally with one or more accessory ingredients. Compressed tablets may be prepared by compressing in a suitable machine, the active ingredients in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredients therein.

5. Bioequivalents

A. Pharmaceutically Acceptable Salts: The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "pharmaceutically acceptable salts" of the penetration enhancers and nucleic acids of the invention and prodrugs of such nucleic acids. "Pharmaceutically acceptable salts" are physiologically and pharmaceutically acceptable salts of the penetration enhancers and nucleic acids of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66:1). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

For oligonucleotides, examples of pharmaceutically acceptable salts include but are not limited to, salts formed with cations such as sodium, potassium, ammonium, magnesium, calcium, polyamines such as spermine and spermidine and the like.

B. Oligonucleotide Prodrugs: The oligonucleotides of the invention may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE ((S-acetyl-2-thioethyl) phosphate) derivatives according to the methods disclosed in WO 93/24510 to Gosselin et al., published Dec. 9, 1993.

C. oligonucleotide Deletion Derivatives: During the process of oligonucleotide synthesis, nucleoside monomers are attached to the chain one at a time in a repeated series of chemical reactions such as nucleoside monomer coupling, oxidation, capping and detritylation. The stepwise yield for each nucleoside addition is above 99%. That means that less than 1% of the sequence chain failed to the nucleoside monomer addition in each step as the total results of the incomplete coupling followed by the incomplete capping, detritylation and oxidation (Smith, *Anal. Chem.*, 1988, 60, 381A). All the shorter oligonucleotides, ranging from (n-1), (n-2), etc., to 1-mers (nucleotides), are present as impurities in the n-mer olignucleotide product. Among the impurities, (n-2)-mer and shorter oligonucleotide impurities are present in very small amounts and can be easily removed by chromatographic purification (Warren et al., Chapter 9 In: *Methods in Molecular Biology*, Vol. 26: *Protocols for Oligonucleotide Conjugates*, Agrawal, S., Ed., 1994, Humana Press Inc., Totowa, N.J., pages 233–264). However, due to the lack of chromatographic selectivity and product yield, some (n-1)-mer impurities are still present in the full-length (i.e., n-mer) oligonucleotide product after the purification process. The (n-1) portion consists of the mixture of all possible single base deletion sequences relative to the n-mer parent oligonucleotide. Such (n-1) impurities can be classified as terminal deletion or internal deletion sequences, depending upon the position of the missing base (i.e., either at the 5' or 3' terminus or internally). When an oligonucleotide containing single base deletion sequence impurities is used as a drug (Crooke, *Hematologic Pathology*, 1995, 9, 59), the terminal deletion sequence impurities will bind to the same target mRNA as the full length sequence but with a slightly lower affinity. Thus, to some extent, such impurities can be considered as part of the active drug component, and are thus considered to be bioequivalents for purposes of the present invention.

D. Ribozymes: Synthetic RNA molecules and derivatives thereof that catalyze highly specific endoribonuclease activities are known as ribozymes (see, generally, U.S. Pat. No. 5,543,508 to Haseloff et al., issued Aug. 6, 1996, and U.S. Pat. No. 5,545,729 to Goodchild et al., issued Aug. 13, 1996). The cleavage reactions are catalyzed by the RNA molecules themselves. In naturally occurring RNA molecules, the sites of self-catalyzed cleavage are located within highly conserved regions of RNA secondary structure (Buzayan et al., *Proc. Natl. Acad. Sci. U.S.A.*, 1986, 83:8859; Forster et al., *Cell*, 1987, 50:9). Naturally occurring autocatalytic RNA molecules have been modified to generate ribozymes which can be targeted to a particular cellular or pathogenic RNA molecule with a high degree of specificity. Thus, ribozymes serve the same general purpose as antisense oligonucleotides (i.e., modulation of expression of a specific gene) and, like oligonucleotides, are nucleic acids possessing significant portions of single-strandedness. That is, ribozymes have substantial chemical and functional identity with oligonucleotides and are thus considered to be equivalents for purposes of the present invention.

E. Other Oligonucleotide Compounds: The present invention may be used to prepare pharmaceutical and other formulations of any oligonucleotide compound and is not limited to the specific oligonucleotides described herein. Moreover, the mechanism of action of an oligonucleotide formulated according to the invention does not impact the scope to which the invention may be practiced. Oligonucleotide compounds can exert their effect by a variety of means. One such means is the antisense-mediated direction of an endogenous nuclease, such as RNase H in eukaryotes or RNase P in prokaryotes, to the target nucleic acid (Chiang et al., *J. Biol. Chem.,* 1991, 266, 18162; Forster et al., *Science,* 1990, 249, 783). Another means involves covalently linking a synthetic moiety having nuclease activity to an oligonucleotide having an antisense sequence, rather than relying upon recruitment of an endogenous nuclease. Synthetic moieties having nuclease activity include, but are not limited to, enzymatic RNAS, lanthanide ion complexes, and the like (Haseloff et al., *Nature,* 1988, 334, 585; Baker et al., *J. Am. Chem. Soc.,* 1997, 119, 8749). Regardless of their mechanism of action, such oligonucleotides are considered to be bioequivalents for the purposes of the present invention.

6. Exemplary Utilities of the Invention: The invention is drawn to the alimentary administration of a nucleic acid, such as an oligonucleotide, having biological activity to an animal. By "having biological activity," it is meant that the nucleic acid functions to modulate the expression of one or more genes in an animal as reflected in either absolute function of the gene (such as ribozyme activity) or by production of proteins coded by such genes. In the context of this invention, "to modulate" means to either effect an increase (stimulate) or a decrease (inhibit) in the expression of a gene. Such modulation can be achieved by, for example, an; antisense oligonucleotide by a variety of mechanisms known in the art, including but not limited to transcriptional arrest; effects on RNA processing (capping, polyadenylation and splicing) and transportation; enhancement or reduction of cellular degradation of the target nucleic acid; and translational arrest (Crooke et al., *Exp. Opin. Ther. Patents,* 1996, 6:1).

In an animal other than a human, the compositions and methods of the invention can be used to study the function of one or more genes in the animal. For example, antisense oligonucleotides have been systemically administered to rats in order to study the role of the N-methyl-D-aspartate receptor in neuronal death, to mice in order to investigate the biological role of protein kinase C-α, and to rats in order to examine the role of the neuropeptide Y1 receptor in anxiety (Wahlestedt et al., *Nature,* 1993, 363:260; Dean et al., *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994, 15:250).

The compositions and methods of the invention are also useful therapeutically, i.e., to provide therapeutic, palliative or prophylactic relief to an animal, including a human, having or suspected of having or of being susceptible to, a disease or disorder that is treatable in whole or in part with one or more nucleic acids. The term "disease or disorder" (1) includes any abnormal condition of an organism or part, especially as a consequence of infection, inherent weakness, environmental stress, that impairs normal physiological functioning; (2) excludes pregnancy per se but not autoimmune and other diseases associated with pregnancy; and (3) includes cancers and tumors. The term "having or suspected of having or of being susceptible to" indicates that the subject animal has been determined to be, or is suspected of being, at increased risk, relative to the general population of such animals, of developing a particular disease or disorder as herein defined. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5 In: *Genetic Monitoring and Screening in the Workplace,* OTA-BA-455, U.S. Government Printing Office, Washington, D.C., 1990, pages 75–99). The term "a disease or disorder that is treatable in whole or in part with one or more nucleic acids" refers to a disease or disorder, as herein defined, (1) the management, modulation or treatment thereof, and/or (2) therapeutic, palliative and/or prophylactic relief therefrom, can be provided via the administration of more nucleic acids. In a preferred embodiment, such a disease or disorder is treatable in whole or in part with an antisense oligonucleotide.

EXAMPLES

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

Example 1

Preparation of Oligonucleotides

A. General Synthetic Techniques: Oligonucleotides were synthesized on an automated DNA synthesizer using standard phosphoramidite chemistry with oxidation using iodine. Beta-cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

The synthesis of 2'-O-methyl-(a.k.a. 2'-methoxy-) phosphorothioate oligonucleotides is according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds.

Similarly, 2'-O-propyl-(a.k.a 2'-propoxy-) phosphorothioate oligonucleotides are prepared by slight modifications of this procedure and essentially according to procedures disclosed in U.S. patent application Ser. No. 08/383,666, filed Feb. 3, 1995, which is assigned to the same assignee as the instant application and which is incorporated by reference herein.

The 2'-fluoro-phosphorothioate oligonucleotides of the invention are synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996, both of which are assigned to the same assignee as the instant application and which are incorporated by reference herein. The 2'-fluoro-oligonucleotides are prepared using phosphoramidite chemistry and a slight modification of the standard DNA synthesis protocol (i.e., deprotection was effected using methanolic ammonia at room temperature).

PNA antisense analogs are prepared essentially as described in U.S. Pat. Nos. 5,539,082 and 5,539,083, both of which (1) issued Jul. 23, 1996, (2) are assigned to the same assignee as the instant application and (3) are incorporated herein by reference in their entirety.

Oligonucleotides comprising 2,6-diaminopurine are prepared using compounds described in U.S. Pat. No. 5,506,351 which issued Apr. 9, 1996, and which is assigned to the same assignee as the instant application and incorporated by reference herein, and materials and methods described by Gaffney et al. (*Tetrahedron*, 1984, 40:3), Chollet et al., (*Nucl. Acids Res.*, 1988, 16:305) and Prosnyak et al. (Genomics, 1994, 21:490). Oligonucleotides comprising 2,6-diaminopurine can also be prepared by enzymatic means (Bailly et al., *Proc. Natl. Acad. Sci. U.S.A.*, 1996, 93:13623).

The 2'-methoxyethoxy oligonucleotides of the invention were synthesized essentially according to the methods of Martin et al. (Helv. Chim. Acta, 1995, 78, 486). For ease of synthesis, the 3' nucleotide of the 2'-methoxyethoxy oligonucleotides was a deoxynucleotide, and 2'-O—$CH_2CH_2OCH_3$—cytosines were 5-methyl cytosines, which were synthesized according to the procedures described below.

B. Synthesis of 5-Methyl Cytosine Monomers:

1. 2,2'-Anhydro[1-(β-D-arabinofuranosyl)-5-methyluridine]: 5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to N,N-dimethylformamide (DMF, 300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2. 2'-O-Methoxyethyl-5-methyluridine: 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 148 hours at 155–160° C., the vessel was opened and the solution evaporated to dryness and triturated with methanol (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/methanol (20:5:3) containing 0.5% $Et_3NH$. The residue was dissolved in CH $Cl_2$ (250 mL) and adsorbed onto silica (150 g) prior to loading onto the column. The product was eluted with the packing solvent to give 160 g (63%) of product.

3. 2'-O-Methoxyethyl-5'-O-dimethoxytrityl-5-methyluridine: 2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. High pressure liquid chromatography (HPLC) showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0;5% $Et_3NH$. The pure fractions were evaporated to give 164 g of product. Approximately 20 g additional was obtained from the impure fractions to give a total yield of 183 g (57%).

4. 3'-O-Acetyl-2'-O-methoxyethyl-5'-O-dimethoxytrityl-5-methyluridine: 2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by thin layer chromatography (tlc) by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approximately 90% product). The residue was purified on a 3.5 kg silica gel column and eluted using EtOAc/Hexane (4:1). Pure product fractions were evaporated to yield 96 g (84%).

5. 3'-O-Acetyl-2'-O-methoxyethyl-5'-O-dimethoxytrityl-5-methyl-4-triazoleuridine: A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0–10° C., and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound.

6. 2'-O-Methoxyethyl-5'-O-dimethoxytrityl-5-methylcytidine: A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. Methanol (400 mL) saturated with $NH_3$ gas was added and the vessel heated to 100° C. for 2 hours (thin layer chromatography, tlc, showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

7. $N^4$-Benzoyl-2'-O-methoxyethyl-5'-O-dimethoxytrityl-5-methylcytidine: 2'-O-Methoxyethyl-5'-O-dimethoxytrityl-5-methylcytidine (85 g; 0.134 M) was dissolved in DMF (800 mL) and benzoic anhydride (37.2 g, 0.165 M) was added with stirring. After stirring for 3 hours, tic showed the reaction to be approximately 95% complete. The solvent was evaporated and the residue azeotroped with MeOH (200 mL). The residue was dissolved in CHCl₃ (700 mL) and extracted with saturated NaHCO₃ (2×300 mL) and saturated NaCl (2×300 mL), dried over MgSO₄ and evaporated to give a residue (96 g). The residue was chromatographed on a 1.5 kg silica column using EtOAc/Hexane (1:1) containing 0.5% Et₃NH as the eluting solvent. The pure product fractions were evaporated to give 90 g (90%) of the title compound.

8. N⁴-Benzoyl-2'-O-methoxyethyl-5'-O-dimethoxytrityl-5-methylcytidine-3'-amidite: N⁴-Benzoyl-2'-O-methoxyethyl-5'-O-dimethoxytrityl-5-methylcytidine (74 g, 0.10 M) was dissolved in CH₂Cl₂ (1 L). Tetrazole diisopropylamine (7.1 g) and 2-cyanoethoxy-tetra(isopropyl) phosphite (40.5 mL, 0.123 M) were added with stirring, under a nitrogen atmosphere. The resulting mixture was stirred for 20 hours at room temperature (tic showed the reaction to be 95% complete). The reaction mixture was extracted with saturated NaHCO₃ (1×300 mL) and saturated NaCl (3×300 mL). The aqueous washes were back-extracted with CH₂Cl₂ (300 mL), and the extracts were combined, dried over MgSO₄ and concentrated. The residue obtained was chromatographed on a 1.5 kg silica column using EtOAc\Hexane (3:1) as the eluting solvent. The pure fractions were combined to give 90.6 g (87t) of the title compound.

C. Oligonucleotide Purification: After cleavage from the controlled pore glass (CPG) column (Applied Biosystems) and deblocking in concentrated ammonium hydroxide, at 55° C. for 18 hours, the oligonucleotides were purified by precipitation 2× from 0.5 M NaCl with 2.5 volumes of ethanol followed by further purification by reverse phase high liquid pressure chromatography (HPLC). Analytical gel electrophoresis was accomplished in 20% acrylamide, 8 M urea and 45 mM Tris-borate buffer (pH 7).

D. Oligonucleotide Labeling: Antisense oligonucleotides were labeled in order to detect the presence of and/or measure the quantity thereof in samples taken during the course of the in vivo pharmacokinetic studies described herein. Although radiolabeling by tritium exchange is one preferred means of labeling antisense oligonucleotides for such in vivo studies, a variety of other means are available for incorporating a variety of radiological, chemical or enzymatic labels into oligonucleotides and other nucleic acids.

1. Tritium Exchange: Essentially, the procedure of Graham et al. (*Nucleic Acids Research*, 1993, 21:3737) was used to label oligonucleotides by tritium exchange. Specifically, about 24 mg of oligonucleotide was dissolved in a mixture of 200 uL of sodium phosphate buffer (pH 7.8), 400 uL of 0.1 mM EDTA (pH 8.3) and 200 uL of deionized water. The pH of the resulting mixture was measured and adjusted to pH 7.8 using 0.095 N NaOH. The mixture was lyophilized overnight in a 1.25 mL gasketed polypropylene vial. The oligonucleotide was dissolved in 8.25 uL of β-mercaptoethanol, which acts as a free radical scavenger (Graham et al., *Nucleic Acids Research*, 1993, 21:3737), and 400 uL of tritiated H₂O (5 Ci/gram). The tube was capped, placed in a 90° C. oil bath for 9 hours without stirring, and then briefly centrifuged to remove any condensate from the inside lid of the tube. (As an optional analytical step, two 10 uL aliquots (one for HPLC analysis, one for PAGE analysis) were removed from the reaction tube; each aliquot was added to a separate 1.5 mL standard microfuge tube containing 490 uL of 50 uM sodium phosphate buffer (pH 7.8).) The oligonucleotide mixture is then frozen in liquid nitrogen and transferred to a lyophilization apparatus wherein lyophilization was carried out under high vacuum, typically for 3 hours. The material was then resuspended in mL of double-distilled H₂O and allowed to exchange for 1 hour at room temperature. After incubation, the mixture was again quick frozen and lyophilized overnight. (As an optional analytical step, about 1 mg of the oligonucleotide material is removed for HPLC analysis.) Three further lyophilizations were carried out, each with approximately 1 mL of double-distilled H₂O, to ensure the removal of any residual, unincorporated tritium. The final resuspended oligonucleotide solution is transferred to a clean polypropylene vial and assayed. The tritium labeled oligonucleotide is stored at about −70° C.

2. Other Means of Labeling Nucleic Acids: As is well known in the art, a variety of means are available to label oligonucleotides and other nucleic acids and to separate unincorporated label from the labeled nucleic acid. Double-stranded nucleic acids can be radiolabeled by nick translation or primer extension, and a variety of nucleic acids, including oligonucleotides, are terminally radiolabeled by the use of enzymes such as terminal deoxynucleotidyl transferase or T4 polynucleotide kinase (see, generally, Chapter 3 In: *Short Protocols in Molecular Biology*, 2d Ed., Ausubel et al., eds., John Wiley & Sons, New York, N.Y., pages 3–11 to 3–38; and Chapter 10 In: *Molecular Cloning: A Laboratory Manual*, 2d Ed., Sambrook et al., eds., pages 10.1 to 10.70). It is also well known in the art to label oligonucleotides and other nucleic acids with nonradioactive labels such as, for example, enzymes, fluorescent moieties and the like (see, for example, Beck, *Methods in Enzymology*, 1992, 216:143; and Ruth, Chapter 6 In: *Protocols for Oligonucleotide Conjugates* (*Methods in Molecular Biology*, Volume 26) Agrawal, S., ed., Humana Press, Totowa, N.J., 1994, pages 167–185).

Example 2

Oligonucleotide Targets and Sequences

The invention is drawn to formulations comprising nucleic acids and one or more oral-gastrointestinal mucosal penetration enhancers, and methods of using such formulations. In one embodiment, such formulations are used to study the function of one or more genes in an animal other than a human. In a preferred embodiment, oligonucleotides are formulated into a pharmaceutical composition intended for therapeutic delivery to an animal, including a human. The following tables list, as exemplars, some preferred oligonucleotides intended for therapeutic delivery that may be administered to the oral-gastrointestinal tract according to the compositions and methods of the invention. Such desired oligonucleotides include, but are not limited to, those which modulate the expression of cellular adhesion proteins (Table 1). Other oligonucleotides are designed to modulate the rate of cellular proliferation (Table 2), or to have biological or therapeutic activity against miscellaneous disorders (Table 3) and diseases resulting from eukaryotic pathogens (Table 4), retroviruses including HIV (human immunodeficiency virus; Table 5) or non-retroviral viral viruses (Table 6). Further details regarding the sources of the following oligonucleotides are provided in the Sequence Listing.

TABLE 1

TARGET OLIGONUCLEOTIDES DESIGNED TO MODULATE CELLULAR ADHESION PROTEINS

| Cell Surface Target Protein | Commercial or Common Name (if any) | Target Oligonucleotide Sequence SEQ ID NO: |
|---|---|---|
| ICAM-1 | ISIS 2302 | 1 |
| ICAM-1 | GM1595 | 2 |
| VCAM-1 | ISIS 5847 | 3 |
| VCAM-1 | GM1535 | 4 |
| ELAM-1 | GM1515 to GM1517 | 5, 6, 7 |

TABLE 2

OLIGONUCLEOTIDES DESIGNED TO MODULATE THE RATE OF CELLULAR PROLIFERATION

| Molecular Target | Commercial or Common Name (if any) | Target Oligonucleotide Sequence SEQ ID NO: |
|---|---|---|
| c-myb | MYB-AS | 8 |
| DNA methyl transferase | | 9, 10 |
| vascular endothelial growth factor (VEGF) | | 11, 12, 13, 14, 15, 16, 17, 18, 19, 20 |
| VEGF | HS | 132 |
| VEGF | Vm | 21 |
| bcl-2 | | 22, 23, 24, 25, 26, 27, 28, 29, 30, 31, 32, 33 |
| bcl-2 | BCL-2 | 34 |
| bcl-abl | | 35 |
| PKC-α, -β, -γ & -ζ | oligo$_{antiPKC\alpha}$ | 36 |
| PKC-α | ISIS 3521 | 37 |
| PKC-ζ | | 38 |
| protein kinase A, subunit RI$_m$ | | 39, 40, 41 |
| βARK1 & βARK2 | oligo$_{anti\beta ARK2}$ | 42 |
| Ha-ras | ISIS 2503 | 43 |
| MDR | | 44, 45, 46, 47 |
| MRP | ISIS 7597 | 48 |
| A-raf kinase | ISIS 9069 | 49 |
| c-raf kinase | ISIS 5132 | 50 |

TABLE 3

OLIGONUCLEOTIDES DESIGNED TO HAVE THERAPEUTIC ACTIVITY AGAINST MISCELLANEOUS DISORDERS

| Disorder | Commercial/Common Name (if any) | Oligonucleotide Sequences SEQ ID NO: |
|---|---|---|
| Alzheimer's disease | | 51, 52, 53, 54, 55, 56, 57, 58, 59, 60, 61, 62 |
| Beta-thalassemia | 5'ss & & 3'ss | 63, 64 |

TABLE 4

OLIGONUCLEOTIDES DESIGNED TO HAVE THERAPEUTIC ACTIVITY AGAINST EUKARYOTIC PATHOGENS

| Pathogen/Disease | Commercial/Common Name (if any) | Oligonucleotide Sequences SEQ ID NO: |
|---|---|---|
| Plasmodium/malaria | PSI, PSII PSIII & RI | 65, 66, 67, 68 |
| Schistosoma/ bloodfluke infections | | 69 |

TABLE 5

OLIGONUCLEOTIDES DESIGNED TO HAVE THERAPEUTIC ACTIVITY AGAINST RETROVIRUSES, INCLUDING HIV

| Virus/Molecular Target | Commercial/Common Name (if any) | Oligonucleotide Sequences SEQ ID NO: |
|---|---|---|
| HTLV-III/primer binding site | | 70, 71, 72, 73, 74, 75 |
| HIV-1/gag | GEM 91 | 76 |
| HIV-1/gag | GEM 92, GEM 93 | 77, 78, 79, 80, 81, 82, 83, 84, 85 |
| HIV | AR 177 | 86 |
| HIV/tat, vpr, rev, env, nef | | 87, 88, 89 |
| HIV/pol, env, vir | | 90, 91, 92, 93, 94, 95, 96, 97 |
| HIV-1/tat, rev, env, nef | | 98, 99, 100, 101, 102, 103 |
| HIV/gp120 | ISIS 5320 | 104 |
| Hepatitis C virus | ISIS 6547 | 105 |

TABLE 6

OLIGONUCLEOTIDES DESIGNED TO HAVE THERAPEUTIC ACTIVITY AGAINST NON-RETROVIRAL VIRUSES

| Virus/Molecular Target | Commercial/ Common Name (if any) | Oligonucleotide Sequences SEQ ID NO: |
|---|---|---|
| influenza virus | | 106, 107, 108, 109, 110, 111, 112, 113, 114 |
| Epstein-Barr Virus | | 115, 116, 117 |
| Respiratory Syncytial Virus | | 118, 119, 120, 121 |
| cytomegalovirus (CMV) | GEM 132 | 122 |
| CMV | | 123, 124, 125, 126, 127, 128, 129, 130 |
| CMV | ISIS 2922 | 131 |

Example 3

Preparation of Formulations Comprising Oligonucleotides and Fatty Acids

Various fatty acids and their derivatives act as penetration enhancers. These include, for example, oleic acid, a.k.a. cis-9-octadecenoic acid (or a pharmaceutically acceptable salt thereof, e.g., sodium oleate or potassium oleate); caprylic acid, a.k.a. n-octanoic acid (caprylate); capric acid, a.k.a. n-decanoic acid (caprate); lauric acid (laurate); acyl-carnitines; acylcholines; and mono- and di-glycerides (Lee et al., *Critical Reviews in Therapeutic Drug Carrier Systems*, 1991, page 92). In order to evaluate the ability of various fatty acids to enhance the oral delivery and/or mucosal penetration of oligonucleotides, the following formulations were prepared.

Reagents: Sources of chemical reagents were as follows.

TABLE 7

Sources of Fatty Acids

| Compound Name | Abbreviation | Supplier |
|---|---|---|
| Capric acid, Na salt | caprate | Sigma* |
| Lauric acid, Na salt | laurate | Sigma |

*Sigma is the Sigma Chemical Company, St. Louis, MO.

Preparations: As an initial screen to evaluate the oligonucleotide penetration enhancing capacity of various fatty acids, several formulations (Table 8) of ISIS 2302 (SEQ ID NO:1) were prepared as follows. Unless otherwise indicated, all percentages are weight per volume (w/v).

TABLE 8

Formulations 1–3

| Formulation No. | ISIS 2302 | Penetration Enhancer(s) |
|---|---|---|
| 1 | 1 mg/ml | 1% laurate |
| 2 | 1 mg/ml | 1% caprate |
| 3 | 1 mg/ml | 0.5% laurate + 0.5% caprate |

Buffer: In a volumetric flask, the following were combined: 14.33 g dibasic sodium phosphate, heptahydrate (U.S.P.); 1.73 g monobasic sodium phosphate, monohydrate (U.S.P.); and 4.4 g sodium chloride (U.S.P.). The volume was brought to 1 l with purified, deionized water. The buffer has a pH of 7.4 and an osmolality of approximately 290 mOsm/kg.

ISIS 2302 Stock Solution: In 30 ml of purified, deionized water, 10 g of pure, anhydrous ISIS 2302 (SEQ ID NO:1) was dissolved. The solution was adjusted to pH 7.4 with 1.0 N NaOH. The volume was adjusted to 50 ml with purified water to yield a final concentration of 200 mg/ml of oligonucleotide ISIS 2302.

Formulation 1: First, 500 mg of sodium laurate was transferred to a 50 ml volumetric flask containing about 40 ml buffer. An aliquot of 250 ul of ISIS 2302 solution was then added to the buffer solution. The solution was titrated to pH 7.4 with 0.1 N HCl, and the volume of the solution was adjusted to 50 ml with buffer.

Formulation 2: First, 500 mg of sodium caprate was transferred to a 50 ml volumetric flask containing about 40 ml buffer. Then, an aliquot of 250 ul of ISIS 2302 solution (200 mg/ml) was added to the buffer solution. The solution was titrated to about pH 7.7 with 0.1 N HCl, and the volume of the solution was adjusted to 50 ml with buffer.

Formulation 3: First, 250 mg of sodium laurate and 250 mg of sodium caprate were transferred to a 50 ml volumetric flask containing about 40 ml buffer. An aliquot of 250 ul of ISIS 2302 solution was then added to the buffer solution. The solution was titrated to pH 7.4 with 0.1 N HCl, and the volume of the solution was adjusted to 50 ml with buffer.

Example 4

Evaluation of Formulations Comprising Fatty Acid Penetration Enhancers by In Situ Perfusion of Rat Ileum Formulations comprising fatty acid penetration enhancers were evaluated as follows.

Methods: In order to evaluate formulations comprising various fatty acids as potential penetration enhancers, in situ perfusion of rat ileum was performed essentially according to the procedure of Komiya et al. (*Int. J. Pharmaceut.*, 1980, 4:249). Specifically, male Sprague Dawley rats weighing 250–300 g were used for the study. After overnight fasting, the rats were anesthetized with 5% pentobarbital (50 mg/kg) by intraperitoneal injection. After a midline abdominal incision was made, the small intestine was taken out and ileum section was located. An incision was made at each end of a 20 cm ileum segment. The ileum segment was laid out in a uniform multiple-S arrangement with 3 bends. The luminal contents of the section were flushed with buffer. A 10 cm piece of silicon rubber tubing was inserted into the intestinal lumen at each incision and ligated with 3-0 silk suture. The proximal end tubing was connected to a 30 mL syringe containing oligonucleotide solution. The solution was perfused through the intestinal segment by using Sage model 365 syringe pump at 0.125 mL/min. The outflow solution was collected in a 2 mL centrifuge tube over 5 min intervals for 80 mins. At the end of perfusion study, an aliquot of 0.3 mL blood sample was collected from the portal vein.

ISIS 2302 concentration in the solution before and after passing through a 20 cm ileum segment was analyzed by high pressure liquid chromatography (HPLC) while the plasma samples were analyzed by capillary electrophoresis (CE). In most cases, tritium labeled ISIS 2302 was used as a tracer and the radioactivity of solution was measured by liquid scintillation counter. The amount of the drug absorbed from the ileum was calculated by dividing the concentration from the average of last six outflow samples (steady state) to that of the inflow sample.

Results: No significant amount (i.e., ~0%) of ISIS 2302 (SEQ ID NO:1) was absorbed at steady state when a control solution (i.e., one lacking any penetration enhancers) was used. In contrast, approximately 5% of ISIS 2302 was absorbed at steady state with a 20 cm ileum segment when Formulations 1 or 2 were perfused. The absorption increased to 15% when Formulation 3 was used. The amounts absorbed was reflected in blood samples collected from the portal veins of the rats. The plasma concentration of ISIS 2302 was 0.29 ug/ml with Formulation 1 and increased to 2.83 ug/ml with Formulation 3.

Example 5

Preparation of Formulations Comprising Oligonucleotides and Bile Salts

The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Goodman et al., eds., McGraw-Hill, New York, N.Y., 1996, pages 934–935). Various natural bile salts, and their synthetic derivatives, act as penetration enhancers. These include, for example, cholic acid, a.k.a. cholalic acid or 3α,7α,12α-trihydroxy-5β-cholan-24-oic acid (or its pharmaceutically acceptable sodium salt); deoxycholic acid, a.k.a. desoxycholic acid, 5β-cholan-24-oic acid-3α,12α-diol, 7-deoxycholic acid or 3α,12α-dihydroxy-5β-cholan-24-oic acid (sodium deoxycholate); glycocholic acid, a.k.a. N-[3α,7α,12α-trihydroxy-24-oxocholan-24-yl]glycine or 3α,7α,12α-trihydroxy-5β-cholan-24-oic acid N-[carboxymethyl]amide (sodium glycocholate); glycodeoxycholic acid, a.k.a. 5β-cholan-24-oic acid N-[carboxymethyl]amide-3α,12α-diol, 3α,12α-dihydroxy-5β-cholan-24-oic acid N-[carboxymethyl]amide, N-[3α,12α-dihydroxy-24-oxocholan-24-yl]glycine or glycodesoxycholic acid (sodium glycodeoxycholate); taurocholic acid, a.k.a. 5β-cholan-24-oic acid N-[2-sulfoethyl]amide-3α,7α,12α-triol, 3α,7α,12α-trihydroxy-5β-cholan-24-oic acid N-[2-sulfoethyl]amide or 2-[(3α,7α,12α-trihydroxy-24-oxo-5β-cholan-24-yl)amino]ethanesulfonic acid (sodium taurocholate); taurodeoxycholic acid, a.k.a. 3α,12α-dihydroxy-Sp-cholan-2-oic acid N[2-sulfoethyl]amide or 2-[(3α,12α-dihydroxy-24-oxo-5β-cholan-24-yl)-amino]ethanesulfonic acid (sodium taurodeoxycholate, a.k.a. sodium taurodesoxycholate); chenodeoxycholic acid, a.k.a. chenodiol, chenodesoxycholic acid, 5β-cholanic acid-3α, 7α-diol or 3α,7α-dihydroxy-5β-cholanic acid (sodium chenodeoxycholate); ursodeoxycholic acid, a.k.a. 5β-cholan-24-oic acid-3α,7α-diol, 7β-hydroxylithocholic acid or 3α,7β-dihydroxy-5β-cholan-24-oic acid; sodium taurodihydro-fusidate (STDHF); and sodium glycodihydro-fusidate (Lee et al., *Critical Reviews in Therapeutic Drug Carrier Systems,* 1991, page 92; Swinyard, Chapter 39 In: *Remington's Pharmaceutical Sciences,* 18th Ed., Gennaro, ed., Mack Publishing Co., Easton, Pa., 1990, pages 782–783). In order to evaluate the ability of various bile salts to enhance the oral delivery and/or mucosal penetration of oligonucleotides, the following formulations (Table 10) were prepared.

Reagents: Sources of chemical reagents were as follows.

TABLE 9

Sources of Bile Salts

| Compound Name | Abbreviation | Supplier |
| --- | --- | --- |
| Cholic acid, Na salt | CA | Sigma[†] |
| Glycholic acid, Na salt | GCA | Sigma |
| Glycodeoxycholic acid, Na Salt | GDCA | Sigma |
| Taurocholic acid, Na salt | TCA | Sigma |
| Taurodeoxycholic acid, Na salt | TDCA | Sigma |
| Chenodeoxycholic acid, Na salt | CDCA | Sigma |
| Ursodeoxycholic acid | UDCA | Aldrich[‡] |

[†]Sigma, Sigma Chemical Company, St. Louis, MO.
[‡]Aldrich, Aldrich Chemical Company, Milwaukee, WI.

TABLE 10

Formulations 4–14

| Formulation No. | ISIS 2302 | Penetration Enhancer(s) |
| --- | --- | --- |
| 4 | 1 mg/ml | 2% GCA |
| 5 | 1 mg/ml | 2% GDCA |
| 6 | 1 mg/ml | 2% TCA |
| 7 | 1 mg/ml | 2% TDCA |
| 8 | 1 mg/ml | 2% CDCA |
| 9 | 1 mg/ml | 2% CA |
| 10 | 1 mg/ml | 1% CDCA + 1% CA |
| 11 | 1 mg/ml | 1% CDCA + 1% GDCA |
| 12 | 1 mg/ml | 1% CDCA + 1% TDCA |
| 13 | 1 mg/ml | 1% TDCA + 1% GDCA |
| 14 | 1 mg/ml | 1% CDCA + 1% UDCA |

Formulation 4: First, 1.0 g of GCA was transferred to a 50 ml volumetric flask containing about 35 ml buffer. An aliquot of 250 ul of ISIS 2302 solution (200 mg/ml) was then added to the buffer solution. The solution osmolality was adjusted to 300 mOsm/kg with of purified, deionized water, and the volume of the solution was adjusted to 50 ml with buffer.

Formulation 5: First, 1.0 g of GDCA was transferred to a 50 ml volumetric flask containing about 35 ml buffer. Then, an aliquot of 250 ul of ISIS 2302 solution (200 mg/ml) was added to the buffer solution. The solution osmolality was adjusted to 300 mOsm/kg with of purified, deionized water, and the volume of the solution was adjusted to 50 ml with buffer.

Formulation 6: First, 1.0 g of TCA was transferred to a 50 ml volumetric flask containing about 35 ml buffer. An aliquot of 250 ul of ISIS 2302 solution (200 mg/ml) was then added to the buffer solution. The solution osmolality was adjusted to 300 mOsm/kg with of purified, deionized water, and the volume of the solution was adjusted to 50 ml with buffer.

Formulation 7: First, 1.0 g of TDCA was transferred to a 50 ml volumetric flask containing about 35 ml buffer. An aliquot of 250 ul of ISIS 2302 solution (200 mg/ml) was then added to the buffer solution. The solution osmolality was adjusted to 300 mOsm/kg with of purified, deionized water, and the volume of the solution was adjusted to 50 ml with buffer.

Formulation 8: First, 1.0 g of CDCA was transferred to a 50 ml volumetric flask containing about 35 ml buffer. Then, an aliquot of 250 ul of ISIS 2302 solution (200 mg/ml) was added to the buffer solution. The solution osmolality was adjusted to 300 mOsm/kg with of purified, deionized water, and the volume of the solution was adjusted to 50 ml with buffer.

Formulation 9: First, 1.0 g of CA was transferred to a 50 ml volumetric flask containing about 35 ml buffer. An aliquot of 250 ul of ISIS 2302 solution (200 mg/ml) was then added to the buffer solution. The solution osmolality was adjusted to 300 mOsm/kg with of purified, deionized water, and the volume of the solution was adjusted to 50 ml with buffer.

Formulation 10: First, 0.5 g of CDCA and 0.5 g of CA were transferred to a 50 ml volumetric flask containing about 35 ml buffer. Then, an aliquot of 250 ul of ISIS 2302 solution (200 mg/ml) was added to the buffer solution. The solution osmolality was adjusted to 300 mOsm/kg with of purified, deionized water, and the volume of the solution was adjusted to 50 ml with buffer.

Formulation 11: First, 0.5 g of CDCA and 0.5 g of GDCA were transferred to a 50 ml volumetric flask containing about 35 ml buffer. An aliquot of 250 ul of ISIS 2302 solution (200 mg/ml) was then added to the buffer solution. The solution osmolality was adjusted to 300 mOsm/kg with of purified, deionized water, and the volume of the solution was adjusted to 50 ml with buffer.

Formulation 12: First, 0.5 g of CDCA and 0.5 g of TDCA were transferred to a 50 ml volumetric flask containing about 35 ml buffer. An aliquot of 250 ul of ISIS 2302 solution (200 mg/ml) was then added to the buffer solution. The solution osmolality was adjusted to 300 mOsm/kg with of purified, deionized water, and the volume of the solution was adjusted to 50 ml with buffer.

Formulation 13: First, 0.5 g of TDCA and 0.5 g of GDCA were transferred to a 50 ml volumetric flask containing about 35 ml buffer. Then an aliquot of 250 ul of ISIS 2302 solution (200 mg/ml) was added to the buffer solution. The solution osmolality was adjusted to 300 mOsm/kg with of purified, deionized water, and the volume of the solution was adjusted to 50 ml with buffer.

Formulation 14: First, 0.5 g of CDCA was transferred to a 50 ml volumetric flask containing about 35 ml buffer and dissolved. Then, 0.5 g UDCA was added to the solution (this modification to the general formulation procedure was necessary because the sodium salt of UDCA is not currently commercially available). An aliquot of 250 ul of ISIS 2302 solution (200 mg/ml) was added to the buffer solution. The solution osmolality was adjusted to 300 mOsm/kg with of purified, deionized water, and the volume of the solution was adjusted to 50 ml with buffer.

Example 6

Evaluation of Formulations Comprising Bile Salt Penetration Enhancers by In Situ Perfusion of Rat Ileum In order to evaluate formulatons comprising various bile salts as potential penetration enhancers, in situ perfusion of rat ileum was performed essentially according to the procedure of Komiya et al. (Int. *J. Pharmaceut.,* 1980, 4:249) as in Example 4.

Results: The results of the evaluations are summarized in Table 11. No significant amount (i.e., ~0%) of ISIS 2302 (SEQ ID NO:1) was absorbed at steady state when a control solution (i.e., one lacking any penetration enhancers) was used. In contrast, about 13% to 28% of ISIS 2302 (SEQ ID NO:1) was absorbed at steady state when 2% of a single bile salt was used as a penetration enhancer (Formulations 4 through 9). The absorption generally increased when a combined bile salt solution was perfused. The blood samples collected from the portal vein at the end of perfusion were scattered. However, the highest blood concentration of ISIS 2302 was observed when solutions of 1% CDCA and 1% UDCA (combination of bile salts) or 2% CDCA (single bile salt) were used.

Example 7

Complex Formulations

Complex formulations (i.e., comprising two or more types of penetration enhancers, e.g., both bile salts and fatty acids) of ISIS 2302 were prepared as follows (see Table 12).

TABLE 11

Enhancement of Oligonucleotide Uptake Due to Bile Salts

| Enhancer(s) | Formulation No. | % Absorption (Mean ± S.D.) | Blood Concentration (Portal Vein) (ug/ml, Mean ± S.D.) |
|---|---|---|---|
| 2% GCA | 4 | 13.3 ± 1.5 | 3.46 ± 1.98 |
| 2% GDCA | 5 | 20.3 ± 7.4 | 0.70 ± 0.0 |
| 2% TCA | 6 | 2.0 ± 1.0 | 0.15 ± 0.21 |
| 2% TDCA | 7 | 14.8 ± 4.2 | 3.65 ± 0.49 |
| 2% CDCA | 8 | 28.4 ± 5.0 | 6.67 ± 2.58 |
| 2% CA | 9 | 13.0 ± 2.8 | 1.65 ± 0.50 |
| 1% CDCA & 1% CA | 10 | 31.0 ± 5.7 | 4.90 ± 1.56 |
| 1% CDCA & 1% GDCA | 11 | 26.3 ± 5.7 | 2.00 ± 0.44 |
| 1% CDCA & 1% TDCA | 12 | 29.7 ± 2.5 | 2.77 ± 2.98 |
| 1% TDCA & 1% GDCA | 13 | 16.5 ± 0.7 | 1.55 ± 0.49 |
| 1% CDCA & 1% UDCA | 14 | 26.0 ± 3.6 | 12.87 ± 3.84 |

TABLE 12

Complex Formulations 15–17

| Formulation No. | ISIS 2302 | Penetration Enhancers |
|---|---|---|
| 15 | 1 mg/ml | 2% CDCA + 0.5% Caprate + 0.5% Laurate |
| 16 | 1 mg/ml | 0.5% CDCA + 1% Caprate + 1% Laurate |
| 17 | 1 mg/ml | 1% CDCA + 1% UDCA + 0.5% Caprate + 0.5% Laurate |

Formulation 15: First, 1.0 g CDCA was transferred to a 50 ml volumetric flask containing about 30 ml of buffer and mixed well. Then, 250 mg sodium caprate and 250 mg sodium laurate were added to the flask. An aliquot of 250 ul of ISIS 2302 stock solution (200 mg/ml) was added to the solution, and the osmolality of the solution was adjusted to 300 mOsm/kg with purified, deionized water. Finally, the volume of the solution was adjusted to 50 ml with buffer.

Formulation 16: First, 250 mg CDCA was transferred to a 50 ml volumetric flask containing about 30 ml of buffer and mixed well. Then, 500 mg sodium caprate and 500 mg sodium laurate were added to the flask. An aliquot of 250 ul of ISIS 2302 stock solution (200 mg/ml) was added to the solution, and the osmolality of the solution was adjusted to 300 mOsm/kg with purified, deionized water. Finally, the volume of the solution was adjusted to 50 ml with buffer.

Formulation 17: First, 500 mg CDCA was transferred to a 50 ml volumetric flask containing about 30 ml of buffer and mixed well. Then, 500 mg UDCA was added to the solution and dissolved by mixing. Next, 250 mg sodium caprate and 250 mg sodium laurate were added to the solution and dissolved via further mixing. An aliquot of 250 ul of ISIS 2302 stock solution (200 mg/ml) was added to the solution, and the osmolality of the solution was adjusted to 300 mOsm/kg with purified, deionized water. Finally, the volume of the solution was adjusted to 50 ml with buffer.

Example 8

Evaluation of Complex Formulations by In Situ Perfusion of Rat Ileum

In order to evaluate formulations comprising various bile salts as potential penetration enhancers, in situ perfusion of rat ileum was performed essentially according to the procedure of Komiya et al. (Int. *J. Pharmaceut.*, 1980, 4:249) as in Example 4.

Results: No significant amount (i.e., ~0%) of ISIS 2302 (SEQ ID NO:1) was absorbed at steady state when a control solution (i.e., one lacking any penetration enhancers) was used. In contrast, the absorption of ISIS 2302 from a 20 cm rat ileum segment ranged from about 31%, about 20% and about 23% (Formulations 15, 16 and 17, respectively) when bile salts and fatty acids were used in combination (Table 13). The blood concentration for samples collected from the portal vein at the end of the perfusion also increased significantly, with values ranging from about 14 ug/ml, about 36 ug/ml and about 15 ug/ml (Formulations 15, 16 and 17, respectively).

TABLE 13

Enhancement of Oligonucleotide Uptake Due to Complex Formulations

| Penetration Enhancers | Formulation No. | % Absorption Mean ± S.D. | Blood Concentration (Portal Vein) (ug/ml, Mean ± S.D.) |
|---|---|---|---|
| 2% CDCA + 0.5% Caprate + 0.5% Laurate | 15 | 30.6 ± 6.4 | 14.32 ± 5.89 |
| 0.5% CDCA + 1% Laurate + 1% Caprate | 16 | 19.7 ± 3.2 | 35.83 ± 11.38 |
| 1% CDCA + 1% UDCA + 0.5% Laurate + 0.5% Caprate | 17 | 23.0 ± 1.4 | 15.4 ± 2.12 |

Example 9

Concentration Effects

Methods: In order to evaluate the effect(s) of varying the concentration of either the penetration enhancer or the active agent (ISIS 2302, SEQ ID NO:1) of the formulations of the invention, the following experiments were performed. In one set of formulations, CDCA (2%) was used as the penetration enhancer for ISIS 2302, the concentration of which was, depending on the formulation, 1, 5, or 10 mg/ml. In another set of formulations, the concentration of ISIS 2302 was held constant at 1 mg/ml and the concentration of the penetration enhancer CDCA was, depending on the formulation, 0.5, 1.0 or 2.0% (w/v). In situ perfusion of rat ileum, as described in Example 4, was then performed using the two sets of formulations.

Results: In the presence of 2% CDCA, the percentage of ISIS 2302 absorbed from a 20 cm rat ileum segment is fairly constant (i.e., about 25% to 28%) in the concentration range from 1 mg/ml to 10 mg/ml. The blood concentration of ISIS 2302, measured in the portal vein, increased from 6.9 ug/ml (1 mg/ml perfusion solution) to 130 mg/ml (10 mg/ml perfusion solution). The amount of ISIS 2302 absorbed from a 20 cm rat ileum segment showed no significant changes when the CDCA concentration was increased from 0.5% to 2%.

Example 10

Bioavailability of Formulations After In Vivo (Intrajejunum) Instillation

In order to evaluate the absolute oral bioavailability of ISIS 2302 formulations containing various penetration enhancers, in vivo intrajejunum instillation was performed with the following formulations (Table 14).

Formulation 18: First, 100 mg CDCA was transferred to a 5 ml volumetric flask containing about 3 ml of buffer. The flask was shaken until the CDCA was completely dissolved. Next, 200 mg sodium caprate and 200 mg sodium laurate were added to the solution, and the flask was shaken until all of the solid material was completely dissolved. Then, 0.5 ml of ISIS 2302 stock solution (200 mg/ml) was added to the solution. Finally, the volume of the solution was adjusted to 5 ml with buffer.

Formulation 19: First, 200 mg sodium caprate and 200 mg sodium laurate were transferred to a 5 ml volumetric flask containing about 3 ml of buffer. Then, 100 mg of UDCA was added and the flask was shaken until the UDCA was completely dissolved. Then, 0.5 ml of ISIS 2302 stock solution (200 mg/ml) was added to the solution. Finally, the volume of the solution was adjusted to 5 ml with buffer.

Formulation 20: As a control, a microemulsion of ISIS 2302 was prepared essentially according to the procedures of Panayiotis (*Pharm. Res.,* 1984, 11:1385). An aliquot of 0.6 ml of ISIS 2302 stock solution (200 mg/ml) was transferred to a 30 ml beaker containing 1.0 ml of Tween 80 (Sigma Chemical Company St. Louis, Mo.). Next, a mixture of 6.3 ml of Captex 355 (Abitec Corp., Janesville, Wis.) and 2.1 ml of Capmul MCM (Abitec Corp., Janesville, Wis.) was added to the beaker. The resultant solution was stirred until a clear solution was formed.

TABLE 14

Intrajejunum Formulations 18–20

| Formulation No. | ISIS 2302 | Penetration Enhancer(s) |
|---|---|---|
| 18 | 20 mg/ml | CDCA 20 mg/ml<br>Caprate 40 mg/ml<br>Laurate 40 mg/ml |
| 19 | 20 mg/ml | UDCA 20 mg/ml<br>Caprate 40 mg/ml<br>Laurate 40 mg/ml |
| 20 | 12 mg/ml | Microemulsion |

Methods: Sprague-Dawley rats weighing 250–300 g were used. After overnight fasting, the rats were anesthetized with 5% pentobarbital (50 mg/kg) by intraperitoneal injection. After a midline abdominal incision was made, the small intestine was pulled out and injection site was located (2 cm after the ligament of Treitz). The intestine was put back to the body carefully. An aliquot of 1.0 mL drug solution was then injected via a 27 gauge needle. Muscle was then surgically closed and skin was clipped after injection. Three hundred uL of blood was collected from a cannula at each sampling time point. The rats were sacrificed in the $CO_2$ chamber 24 hours after dosing. Livers and kidneys were excised and stored at −80° C. until analysis. Radioactivity of plasma and tissue samples were measured. Liver and kidney were also analyzed for oligonucleotide content by CE.

Results: The results of study are summarized in Table 15. No significant amount (i.e., ~0%) of ISIS 2302 (SEQ ID NO:1) was absorbed at steady state when a control solution (i.e., one lacking any penetration enhancers) was used. In contrast, the absolute bioavailability was in the range of 8 to 29% in the examined target organs (livers and kidneys). The AUC(0–3 h) shows 10–13% bioavailability. However, it should be noted that the AUC(0–3 h) comparison tends to underestimate the bioavailability, since the blood concentration from the intestinal instillation is much higher than that from i.v. injection at 3 hours after dosing.

TABLE 15

Percent Absolute Bioavailability (% i.v.) of ISIS 2302 After Jejunum Instillation in Rats

| Formulation No. (Dose) | Liver[1] | Kidney[1] | AUC(0–3 h) (ug × h/mL)[2] |
|---|---|---|---|
| Formulation 18 (80 mg/kg) | 17.4 | 17.8 | 10.7 |
| Formulation 19 (80 mg/kg) | 8.8 | 23.0 | 13.5 |
| Formulation 20 (48 mg/kg) | 19.8 | 29.1 | 13.6 |

[1]According to the CE analysis - total oligonucleotide.
[2]According to analysis by radioactivity. AUC(0–3 h) was calculated for all in vivo instillation studies because the results from radioactivity measurements are comparable to those from HPLC analyses for the first 3 hour plasma samples.

Example 11

Dose Proportionality After In Vivo Jejunal and Colonic Instillation of Oligonucleotides in Rats In order to evaluate the amount of ISIS 2302 absorbed as a function of dose after jejunal and colonic instillation in rats, the following studies were performed.

Methods: Sprague-Dawley rats weighing 250–300 g were used. After overnight fasting, the rats were anesthetized with 5% pentobarbital (50 mg/kg) by intraperitoneal injection. After a midline abdominal incision was made, the small intestine was pulled out and the injection site was located (2 cm after the ligament of Treitz for jejunum and 1 cm after the ileocecal junction for colon). The intestine was put back into the body carefully. An aliquot of 1.0 mL (jejunum) or 0.5 mL (colon) drug solution was injected via a 27 gauge needle. Muscle was then surgically closed and skin was clipped after injection. Three hundred uL of blood was collected from femoral vein at 0.5, 1, 2, and 3 hours after dosing. Rats were sacrificed after a period of three hours for sample collection.

Formulations: The concentration of enhancers remained constant (2% CDCA, 4% laurate and 4% caprate) for the study. The concentration of ISIS 2302 ranged from 10 mg/mL to 80 mg/mL for jejunal instillation and from 33.4 mg/mL to 120 mg/mL for colonic instillation. Formulations were prepared according to the procedures of the previous Examples.

Results: Results of the study are summarized in Table 16. No significant amount (i.e., ~0%) of ISIS 2302 (SEQ ID NO:1) was absorbed at steady state when a control solution (i.e., one lacking any penetration enhancers) was used. In contrast, the AUC(0–2 h) of ISIS 2302 increased proportionally in the concentration range studied for the jejunal instillation. The AUC(0–2 h) of ISIS 2302 increased initially (from 16.7 mg to 28.6 mg) and reached a plateau region when 30 mg and 60 mg of ISIS 2302 was given colonically.

TABLE 16

Results of In Vivo Jejunal and Colonic Instillation of Oligonucleotides in Rats

| Jejunal Dose (mg/rat) | Jejunal AUC(0–2 h) (µg × h/mL) | Colonic Dose (mg/rat) | Colonic AUC(0–2 h) (µg × h/mL) |
|---|---|---|---|
| 10 | 39.98 | 16.7 | 29.45 |
| 20 | 65.33 | 28.6 | 101.29 |
| 40 | 105.89 | 60.0 | 91.7 |
| 80 | 193.78 | | |

Example 12

Combinations of Specific Oligonucleotide Chemistries and Formulations Resulting in Enhanced Oral Bioavailability In order to evaluate the effect of oligonucleotide chemistries on bioavailability using the formulations of the invention, the following experiments were carried out. Several oligonucleotide compounds targeted to human ICAM-1 and having the same nucleobase sequence, but varying in terms of chemical modifications, were administered to rats by intrajejunal instillation essentially according to the procedure described in the preceding Examples. All of the following isosequence oligonucleotides have uniform phosphorothioate backbones and all have SEQ ID NO:1 (5'-GCCCAAGCTGGCATCCGTCA-3'). More specifically, the antisense compounds used in these studies are:

1. ISIS 2302: GCCCAAGCTGGCATCCGTCA (SEQ ID NO:1)

ISIS 2302 is a fully 2'-deoxyoligonucleotide containing no 2'-methoxyethoxy or 5-methylcytidine residues.

2. ISIS 14725: GCCCAAGCTGGCATCCGTCA (SEQ ID NO:1)

ISIS 14725 is a "hemimer"; emboldened and double-underlined residues are 2'-methoxyethoxy (2'-MOE) modified. All 2'-MOE cytidines are 5-methylcytidine (m5c) as indicated by the double-underlined "C" characters.

3. ISIS 15839: GCCCAAGCTGGCATCCGTCA (SEQ ID NO:1)

ISIS 15839 is a fully m5c "hemimer"; emboldened residues are 2'-methoxyethoxy (2'-MOE) modified. All cytidines (including 2'-deoxycytidines) are 5-methylcytidine (m5c) as indicated by the double-underlined "C" and "C" characters.

Oligonucleotides were administered to rats at 40 mg/kg in a volume of 0.5 mL, with and without penetration enhancer (s). Plasma samples were taken at 0.5, 1.0, 2.0 and 3.0 hours; tissue samples were taken 24 hours after dosing. Oligonucleotide concentration in the tissue samples was measured, and % bioavailability was calculated, as described in the preceding Examples.

The results (Table 17) show that a formulation comprising 2% of the bile salt CDCA and the fully {C->m5c}-substituted 2'-methoxyethoxy hemimer ISIS 15839 resulted in about 18% bioavailability in plasma, compared to 11% bioavailability in plasma when the same formulation was used with ISIS 2302, an isosequence 2'-deoxy, non-m5c oligonucleotide. Moreover, a formulation comprising bile salt (2% CDCA) and fatty acids (4% Na Caprate and 4% Na Laurate) resulted in about 32% bioavailability of ISIS 15389 in plasma, compared to about 15% bioavailability in plasma for ISIS 2302 when the same formulation is used. Compositions comprising oligonucleotides that are partially or fully {C->m5c}-substituted and, additionally or alternatively, comprise one or more 2'-methoxyethoxy modifications, are thus preferred embodiments of the invention.

TABLE 17

In Vivo Bioavailability (BAV)- Plasma AUC or Tissue

| Compound | Formulation | Plasma BAV | Tissue BAV |
|---|---|---|---|
| ISIS 2302 | Water or saline | 1–2% | 1–2% |
| ISIS 2302 | Bile salt (2% CDCA)[1] | 11% | ND[3] |
| ISIS 2302 | Bile salt (2% CDCA) and fatty acids (4% Na caprate + 4% Na laurate)[2] | 14.6% | 18–30% |
| ISIS 14725 | Water or saline | 5–8% | 5.2% |
| ISIS 15839 | Water or saline | ND | ND |
| ISIS 15839 | Bile salt (2% CDCA)[1] | 17.5% | ND |
| ISIS 15839 | Bile salt (2% CDCA) and fatty acids (4% Na caprate + 4% Na laurate)[2] | 31.6% | ND |

[1]Corresponds to Formulation 8.
[2]Corresponds to Formulation 18.
[3]ND, not determined.

Example 13

In Vivo Bioavailability of ICAM-1 Oligonucleotides in Dogs

Dogs were "ported" with intestinal access catheters through which formulated drug formulations (solutions or suspensions) may be introduced into various areas of the gut. Target areas include the proximal jejunum and distal ilium or the ileocecal junction. In addition to ported dogs, naive dogs are used for the assessment of formulations given by conventional routes, e.g., oral administration for oral dosage forms, rectal administration for enema or suppository formulations, etc.

ISIS 2302 and ISIS 15839 were administered intrajejunally to "ported" dogs at oligonucleotide doses of 10 mg/kg with or without penetration enhancers. Specifically, an aliquot of 20 mg/mL drug solution was injected into a subcutaneous port catheter connected to the proximal jejunum. Bile salts (CDCA) were used alone or in combination with fatty acids (2% CDCA, 4% Na caprate, 4% Na laurate). Blood samples were collected from the femoral vein for up to 6 hours and evaluated for the presence and concentration of oligonucleotides by HPLC. Percent bioavailability (% BAV) was calculated as:

$$\frac{\text{intact plasma conc. (AUC) by alimentary administration}}{\text{intact plasma concentration by intravenous administration}} \times 100\%,$$

wherein "AUC" refers to the Area Under the Curve and "conc." indicates concentration.

TABLE 18

Absolute Bioavailability of Oligonucleotides in Dogs After Intrajejunal Administration

| Compound | n | Formulation | % BAV |
|---|---|---|---|
| ISIS 2302 | 2 | Water or saline (no enhancer control) | 0.3% |
| ISIS 2302 | 2 | Bile salt (2% CDCA) only | 1.3% |
| ISIS 2302 | 2 | Fatty acids (4% Na Caprate + 4% Na Laurate) only | 5.4% |
| ISIS 2302 | 3 | Bile salt (2% CDCA) and Fatty acids (4% Na Caprate + 4% Na Laurate) | 8.4% |
| ISIS 15839 | 2 | Water or saline (no enhancer control) | 1.5% |
| ISIS 15839 | 3 | Bile salt (2% CDCA) only | 4.4% |
| ISIS 15839 | 3 | Fatty acids (4% Na Caprate + 4% Na Laurate) only | 2.5% |
| ISIS 15839 | 2 | Bile salt (2% CDCA) and fatty acids (4% Na Caprate + 4% Na Laurate) | 18.0% |

The results (Table 18) confirm and extend the results from the rat experimental systems. Specifically, for the phosphorothioate, non-{C->m5c}-substituted 2'-deoxyoligonucleotide ISIS 2302, the % bioavailability was maximal (8.4%) when formulated with a bile salt (2% CDCA) and fatty acids (4% sodium caprate and 4% sodium laurate). When the same formulation was prepared comprising the phosphorothioate, fully {C->m5c}-substituted, 2'-deoxy-/2'-methoxyethoxy-oligonucleotide ISIS 15839, a greater % bioavailability (18%) resulted.

Example 14

Dose Proportionality Studies of Oligonucleotides in Dogs

Dogs were "ported" with intestinal access catheters as in the previous Example and a series of varying doses of ISIS 15839 were administered. Although the concentration of oligonucleotide varied, the kinds and concentration of penetration enhancers used in these experiments were held constant (2% CDCA.Na, 4% sodium laurate and 4% sodium caprate). Bioavailability (AUC, O-6 h) was determined as in the preceding Examples.

The results (Table 19) show that bioavailability decreases with increasing absolute dose and drug concentration. There is a clear trend of decreasing bioavailability as the oligonucleotide dose was increased, i.e., as the proportion of penetration enhancers was decreased. These results indicate that higher ratios of (penetration enhancer(s)) to [oligonucleotide] are preferred.

TABLE 19

Dose Proportionality of ISIS 15839 in Dogs

| Dose (mg/kg) | Drug Concentration (mg/mL) | % BAV |
|---|---|---|
| 10 | 20 | ~18.0% |
| 20 | 40 | ~7.0% |
| 40 | 80 | ~1.5% |

Example 15

Oligonucleotide: Penetration Enhancer Co-Delivery Studies

It is possible that oligonucleotides and penetration enhancers (PEs) are best delivered contemporaneously to one or more sites for maximal bioavailability if, for example, one or more PEs and an oligonucleotide cross a rate-limiting barrier as a complex. Alternatively, as another example, delivery of PEs to the intestinal lumen prior to the delivery of oligonucleotides might allow the PEs more time to act on the cells of the GI tract than is available when the oligonucleotide and PEs arrive at such cells at the same time; in this case, maximal bioavailability of the oligonucleotide would occur sometime after the administration of the PEs. In order to examine some of the kinetic aspects of oligonucleotide:penetration enhancer effects, the following experiments were carried out.

In a first set of experiments, ISIS 2302 was administered intrajejunally to rats, as in Example 10, at various times after the administration of a formulation of penetration enhancers (2% CDCA.Na, 4% sodium laurate and 4% sodium caprate), and the absolute bioavailability (AUC, 0–3 h) was determined as in the preceding Examples. The results (Table 20) show a general trend towards decreased bioavailability as oligonucleotide is delivered at increasingly longer intervals after delivery of the penetration enhancers. These results indicate that formulations that provide for the concomitant release of oligonucleotide and penetration enhancers at appropriate sites in vivo are preferred.

In a second set of experiments, Dogs were "ported" with intestinal access catheters as in the preceding Examples. ISIS 2302 was administered at various times after the administration of penetration enhancers (2% CDCA.Na, 4% sodium laurate and 4% sodium caprate), and the absolute bioavailability (AUC, 0–6 h) was determined as in the preceding Examples. The results (Table 21) demonstrate the same general trend as was seen in rats; i.e., bioavailability is maximal when the oligonucleotide and penetration enhancer are contemporaneously delivered and decreases when oligonucleotide is delivered after the PE delivery.

TABLE 20

Administration Time Studies in Rats (40 mg/kg ISIS 2302)

| Time After PE Administration Oligonucleotide Deliver | Absolute % BAV (n = 2 or 5) |
|---|---|
| Co-Administration | 14.6 (n = 5) |
| 15 min. | 13.2, 15.2 |
| 30 min. | 9.7, 9.8 |
| 60 min. | 1.4, 8.0 |

TABLE 21

Administration Time Studies in Dogs (10 mg/kg ISIS 2302)

| Time After PE Administration Oligonucleotide Deliver | Absolute % BAV (n = 2) |
|---|---|
| 15 min. | 10, (*) |
| 30 min. | 10, 22 |
| 60 min. | ~0, 25 |

*Data from one animal lost due to leakage at the injection site.

Example 16

Formulations Comprising Acid, or Acid and Salt, Forms of Penetration Enhancers

In the formulations of the preceding Examples, with the exception of UDCA and other indicated exceptions, bile salts have been added to formulations as sodium (Na) salts. As indicated in Example 5, these bile salts are also available in their acid forms. In order to determine if effective oligonucleotide delivery is promoted by the acid forms of bile salts, or by combinations of the acid and salt forms of bile salts, the following studies were carried out.

In order to evaluate the ability of acid forms of bile salts to act as penetration enhancers of oligonucleotides, comparative formulations (Table 22) were prepared according to the methods described in the preceding Examples with the following modifications.

In order to minimize the proportion of water in pharmaceutical formulations, the solvents propylene glycol (PPG 400, Spectrum Quality Products, Inc., Gardena, Calif.) and polyethylene glycol (PEG 400, Spectrum) were tested for their ability to dissolve ISIS 2302. Although the solubility of oligonucleotide in PPG was considerable (i.e., >160 mg/mL), oligonucleotide exhibited only limited solubility in PEG (0.08 mg/ML). Studies demonstrated that the bioavailability of oligonucleotide, alone or in combination with the penetration enhancers of the invention, was not effected by PPG. Thus, PPG was used a solvent in the following formulations. The PPG solutions of oligonucleotides were more viscous than water-based solutions and may provide for lower diffusion rates of oligonucleotide and penetration enhancers in vivo; if so, PPG-based solutions of oligonucleotides are expected to provide for the extended release of oligonucleotides in patients.

Inclusion of PPG in the formulations allows the water content of the formulations to be decreased to less than about 10%, preferably less than about 8% and more preferably less than about 5%. In the following PPG-based formulations, the water content 7.5% unless otherwise indicated.

TABLE 22

Acid/Salt Comparative Formulations of ISIS 2302
Amount of Component in:

| Component | Acid Formula | Salt Formula | Mixed Formula |
|---|---|---|---|
| Lauric Acid | 200 mg | — | 100 mg |
| Sodium Laurate | — | 200 mg | 100 mg |
| Capric Acid | 200 mg | — | 100 mg |
| Sodium Caprate | — | 200 mg | 100 mg |
| UDCA | 100 mg | — | — |
| CDCA | — | — | 50 mg |
| CDCA.Na | — | 100 mg | 50 mg |
| ISIS 2302 | 100 mg | 100 mg | 100 mg |
| $H_2O$ | 375 µL | 375 µL | 375 µL |
| PPG | QS to 5 mL | QS to 5 mL | QS to 5 mL |

These formulations were evaluated in rat (n=3 or 4) by intrajejeunal instillation (0.5 mL, 40 mg/kg). Samples were taken up to 3 hours after administration and the absolute bioavailability (AUC, 3–4 h) was determined.

The results (Table 23) demonstrate the unexpected result that oligonucleotide bioavailability is best enhanced by a formulation having mixtures of the sodium salts and acid forms of bile salts and fatty acids. That is, oligonucleotide bioavailability was about 17% when the Mixed Formulation was used, whereas it was only about 7% and 12% when the Acid or Salt Formulations, respectively, were used.

TABLE 23

Bioavailability of Comparative Formulations

| Formulation | Bioavailability | Range |
|---|---|---|
| Acid | 7.3 ± 0.6% | 6.9% to 8.0% |
| Salt | 12.5 ± 8.1% | 6.0% to 23.2% |
| Mixed | 17.0 ± 1.4% | 15.9% to 18.5% |

Example 17

Preparation of the Sodium Salt of UDCA

When used for gallstone dissolution, CDCA may cause diarrhea, elevated plasma transaminase activity and elevated serum cholesterol. UDCA is as effective for this use at higher doses, but causes diarrhea less frequently and does not later serum cholesterol or plasma transaminase activity (Brunton, Chapter 38 In: *Goodman & Gilman's The Pharmacological Basis of Therapeutics*, 9th Ed., Hardman et al., eds., McGraw-Hill, New York, N.Y., 1996, pages 934–935). Thus, UDCA is used in place of CDCA in some preferred embodiments of the invention.

Ursodeoxycholic acid (UDCA) is commercially available in its acid form (Aldrich Chemical Company, Milwaukee, Wis.) but not as a sodium salt. In order to carry out experiments to evaluate the potential of the sodium salt of UDCA to act as a penetration enhancer, the following novel method of efficiently preparing the sodium salt of UDCA from its acid form was developed.

Step 1:
Dissolve 500 mg UDCA in 2.4 mL ethanol (>99%). (The volume of ethanol volume can be increased slightly with no adverse effect.)

Step 2:
Dissolve 1 g of NaOH in 0.9 mL $H_2O$. (Handle reaction vessels with care, as the process generates heat.)

Step 3:
Slowly transfer 46 µL NaOH solution from step 2 to the solution of step 1 with vigorously constant mixing (The mixing is 1:1 molar ratio).

Notes for Step 3:
(A) The volume of NaOH solution added should not be more than 50 µL; otherwise the UDCA sodium salt will be redissolved.
(B) The concentrated NaOH solution tends to settle at the bottom of the reaction vessel; as a result, constant and vigorous stirring is required during this step.

Step 4:
Filter the solution and wash the precipitate with ethanol to eliminate any remaining UDCA (acid). The precipitate can then be air dry or dried by lyophilization.

In order to determine the ability of the sodium salt of UDCA to act as a penetration enhancer for oligonucleotides, formulations are prepared and tested as in the preceding Examples, except that UDCA.Na is used in place of CDCA.Na.

The disclosure demonstrates that a variety of formulations comprising an oligonucleotide and one or more penetration enhancers result in bioavailabilities that are typically more than about 15%, in a range from about 1.5% to about 35%, most preferably from about 17% to about 35%. Those skilled in the art will be able to prepare numerous equivalent formulations without undue experimentation upon comprehension of the present disclosure.

What is claimed is:

1. A composition comprising a nucleic acid and capric acid and lauric acid, or a nucleic acid and pharmaceutically acceptable salts of capric acid and lauric acid, wherein said nucleic acid has a modified nucleobase or a modified sugar residue.

2. The composition of claim 1 wherein said nucleic acid is an antisense oligonucleotide.

3. The composition of claim 2 wherein said antisense oligonucleotide decreases the expression of a cellular adhesion protein or the rate of cellular proliferation.

4. The composition of claim 1 wherein said nucleic acid has a cytosine to 5-methyl-cytosine substitution or a 2'-methoxyethoxy modification.

* * * * *